US012617772B2

(12) United States Patent
Odingo et al.

(10) Patent No.: US 12,617,772 B2
(45) Date of Patent: May 5, 2026

(54) HYDROXYPYRIDINE HSD17B13 INHIBITORS AND USES THEREOF

(71) Applicant: INIPHARM, INC., Bellevue, WA (US)

(72) Inventors: Joshua Odingo, Bothell, WA (US); Sampath Kumar Anandan, Fremont, CA (US); Heather Kay Webb Hsu, Seattle, WA (US); Vincent Florio, Seattle, WA (US); Subramanyam Janardhan Tantry, Karnataka (IN); Athisayamani Jeyaraj Duraiswamy, Karnataka (IN); Bharathi Mohan Kuppusamy, Karnataka (IN)

(73) Assignee: INIPHARM, INC., Bellevue, WA (US)

( * ) Notice: Subject to any disclaimer, the term of this patent is extended or adjusted under 35 U.S.C. 154(b) by 397 days.

(21) Appl. No.: 18/553,829

(22) PCT Filed: Apr. 4, 2022

(86) PCT No.: PCT/US2022/023350

§ 371 (c)(1),
(2) Date: Oct. 3, 2023

(87) PCT Pub. No.: WO2022/216626

PCT Pub. Date: Oct. 13, 2022

(65) Prior Publication Data

US 2024/0208929 A1 Jun. 27, 2024

Related U.S. Application Data

(60) Provisional application No. 63/170,852, filed on Apr. 5, 2021.

(51) Int. Cl.

| | |
|---|---|
| ***C07D 401/12*** | (2006.01) |
| ***A61K 31/4436*** | (2006.01) |
| ***A61K 31/517*** | (2006.01) |
| ***C07D 409/12*** | (2006.01) |

(52) U.S. Cl.

CPC ........ *C07D 401/12* (2013.01); *A61K 31/4436* (2013.01); *A61K 31/517* (2013.01); *C07D 409/12* (2013.01)

(58) Field of Classification Search

CPC .................................................... C07D 401/12
USPC .................................................... 514/266.22
See application file for complete search history.

(56) References Cited

U.S. PATENT DOCUMENTS

| | | | |
|---|---|---|---|
| 2,694,711 | A | 11/1954 | Randall et al. |
| 6,143,777 | A | 11/2000 | Jonas et al. |
| 11,827,619 | B2 | 11/2023 | Anandan et al. |
| 2006/0217426 | A1 | 9/2006 | Eto et al. |
| 2007/0010537 | A1 | 1/2007 | Hamamura et al. |
| 2008/0255161 | A1 | 10/2008 | Koltun et al. |
| 2009/0023710 | A1 | 1/2009 | Vicker et al. |
| 2012/0165330 | A1 | 6/2012 | Vu |
| 2015/0119426 | A1 | 4/2015 | Marugan et al. |
| 2017/0096435 | A1 | 4/2017 | Tebbe et al. |
| 2019/0330124 | A1 | 10/2019 | DeWitt |
| 2023/0278978 | A1 | 9/2023 | Odingo et al. |
| 2023/0286923 | A1 | 9/2023 | Odingo et al. |
| 2023/0416802 | A1 | 12/2023 | Hsu et al. |
| 2024/0150314 | A1 | 5/2024 | Anandan et al. |
| 2024/0208959 | A1 | 6/2024 | Odingo et al. |

FOREIGN PATENT DOCUMENTS

| | | | |
|---|---|---|---|
| CN | 1233246 | A | 10/1999 |
| CN | 101287728 | A | 10/2008 |
| CN | 102898416 | A | 1/2013 |
| CN | 103288771 | A | 9/2013 |
| CN | 105524053 | A | 4/2016 |
| CN | 107206005 | A | 9/2017 |
| CN | 109563070 | A | 4/2019 |
| CN | 118955491 | A | 11/2024 |
| KR | 20170092126 | A | 8/2017 |
| WO | WO-9722619 | A2 | 6/1997 |
| WO | WO-2006008545 | A2 | 1/2006 |
| WO | WO-2007000655 | A2 | 1/2007 |
| WO | WO-2007003934 | A2 | 1/2007 |
| WO | WO-2007022258 | A1 | 2/2007 |
| WO | WO-2008039489 | A2 | 4/2008 |
| WO | WO-2008127615 | A1 | 10/2008 |
| WO | WO-2011154327 | A1 | 12/2011 |
| WO | WO-2016081522 | A1 | 5/2016 |
| WO | WO-2017121388 | A1 | 7/2017 |
| WO | WO-2018034883 | A1 | 2/2018 |
| WO | WO-2018204775 | A1 | 11/2018 |
| WO | WO-2019154956 | A1 | 8/2019 |
| WO | WO-2019183329 | A1 | 9/2019 |
| WO | WO-2020041741 | A1 | 2/2020 |

(Continued)

OTHER PUBLICATIONS

Co-pending U.S. Appl. No. 18/730,991, inventors Odingo; Joshua et al., filed Jul. 22, 2024.
Beach et al. Structure of nidulin. J. Org. Chem. 26:1339-40 (1961).
Bolon. Oxidative substitution on halophenols. J. Org. Chem. 38(9):1741-2 (1973).
CAS Registry No. 1301072-73-0; STN Entry Date: May 26, 2011; 2-[(3-Chloro-4,5-dimethoxybenzoyl)amino]-N-cyclopropyl-3-thiophenecarboxamide.
CAS Registry No. 1347715-76-7; STN Entry Date: Dec. 2, 2011; 3,5-dichloro-4-hydroxy-N-[2-[[(1-methylethyl)amino]carbonyl]-4-phenoxyphenyl]-benzamide.

(Continued)

*Primary Examiner* — Niloofar Rahmani
(74) *Attorney, Agent, or Firm* — WILSON SONSINI GOODRICH & ROSATI

(57) ABSTRACT

Described herein are hydroxypyridine HSD17B13 inhibitors and pharmaceutical compositions comprising said inhibitors. The subject compounds and compositions are useful for the treatment of liver disease, metabolic disease, or cardiovascular disease, such as NAFLD or NASH, or drug induced liver injury (DILI).

20 Claims, No Drawings

(56) References Cited

FOREIGN PATENT DOCUMENTS

| | | | | |
|---|---|---|---|---|
| WO | WO-2021003295 A1 | | 1/2021 | |
| WO | WO-2022020714 A1 | | 1/2022 | |
| WO | WO-2022020730 A1 | * | 1/2022 | ........... C07D 239/91 |
| WO | WO-2022029210 A1 | | 2/2022 | |
| WO | WO-2022040324 A1 | | 2/2022 | |
| WO | WO-2022072491 A1 | | 4/2022 | |
| WO | WO-2022072512 A1 | | 4/2022 | |
| WO | WO-2022072517 A1 | | 4/2022 | |
| WO | WO-2022103960 A1 | | 5/2022 | |
| WO | WO-2022216626 A1 | | 10/2022 | |
| WO | WO-2022216627 A1 | | 10/2022 | |
| WO | WO-2023023310 A1 | | 2/2023 | |
| WO | WO-2023146897 A1 | | 8/2023 | |
| WO | WO-2023237504 A1 | | 12/2023 | |

OTHER PUBLICATIONS

CAS Registry No. 1349612-23-2; STN Entry Date: Dec. 6, 2011; 3-[[[(1S,9S)-9-[(3,5-dichloro-4-hydroxybenzoyl)amino]octahydro-6, 10-dioxo-6H-pyridazino[1,2-a][1,2]diazepin-1-yl]carbonyl]amino]-4-oxo-butanoic acid Whole document.

CAS Registry No. 1552614-71-7; STN Entry Date: Feb. 23, 2014; N-(3,5-dichloro-4-hydroxyphenyl)-1-(2-methylpropyl)-cyclopentanecarboxamide.

CAS Registry No. 1555050-09-3; STN Entry Date: Feb. 25, 2014; N-(3,5-dichloro-4-hydroxyphenyl)-4-(1,1-dimethylethyl)-1,2,3-thiadiazole-5-carboxamide.

CAS Registry No. 1797791-87-7; STN Entry Date: Jul. 9, 2015; 2-[(3-Chloro-4-ethoxy-5-methoxybenzoyl)amino]-N-cyclopropyl-3-thiophenecarboxamide.

CAS Registry No. 1927122-50-6; STN Entry Date: Jun. 8, 2016; N-(3,5-dichloro-4-hydroxyphenyl)-3-(1,1-dimethylethyl)-1H-1,2,4-triazole-5-carboxamide.

CAS Registry No. 2330771-94-1; STN Entry Date: Jun. 12, 2019; N-(3,5-dichloro-4-hydroxyphenyl)-2-(1,1-dimethylethyl)-4-quinolinecarboxamide.

CAS Registry No. 2330772-10-4; STN Entry Date: Jun. 12, 2019; 6-bromo-N-(3,5-dichloro-4-hydroxyphenyl)-2-(1,1-dimethylethyl)-4-quinolinecarboxamide.

CAS Registry No. 2330848-81-0; STN Entry Date: Jun. 12, 2019; N-(3,5-dichloro-4-hydroxyphenyl)-4-(1,1-dimethylethyl)-benzamide.

CAS Registry No. 2334810-01-2; STN Entry Date: Jun. 16, 2019; 8-bromo-N-(3,5-dichloro-4-hydroxyphenyl)-2-(1,1-dimethylethyl)-4-quinolinecarboxamide.

CAS Registry No. 2338353-08-3; STN Entry Date: Jun. 18, 2019; 8-chloro-N-(3,5-dichloro-4-hydroxyphenyl)-2-(1,1-dimethylethyl)-4-quinolinecarboxamide.

CAS Registry No. 2341653-65-2; STN Entry Date: Jun. 20, 2019; N-(3,5-dichloro-4-hydroxyphenyl)-2-(1,1-dimethylethyl)-2,3-dihydro-1,3-dioxo-1H-isoindole-5-carboxamide.

CAS Registry No. 2341653-72-1; STN Entry Date: Jun. 20, 2019; N-(3,5-dichloro-4-hydroxyphenyl)-2,3-dihydro-2-(1-methylpropyl)-1,3-dioxo-1H-isoindole-5-carboxamide.

CAS Registry No. 2343097-82-3; STN Entry Date: Jun. 23, 2019; N-(3,5-dichloro-4-hydroxyphenyl)-2-(1,1-dimethylethyl)-6-methyl-4-quinolinecarboxamide.

CAS Registry No. 2343990-73-6; STN Entry Date: Jun. 24, 2019; N-(3,5-dichloro-4-hydroxyphenyl)-2-(1,1-dimethylethyl)-6-fluoro-4-quinolinecarboxamide.

CAS Registry No. 2343990-76-9; STN Entry Date: Jun. 24, 2019; 6-chloro-N-(3,5-dichloro-4-hydroxyphenyl)-2-(1,1-dimethylethyl)-4-quinolinecarboxamide.

CAS Registry No. 2346009-72-9; STN Entry Date: Jun. 26, 2019; N-(3,5-dichloro-4-hydroxyphenyl)-1-(1,1-dimethylethyl)-5-oxo-3-pyrrolidinecarboxamide.

CAS Registry No. 2346679-45-4; STN Entry Date: Jun. 27, 2019; N-(3,5-dichloro-4-hydroxyphenyl)-2-(1,1-dimethylethyl)-8-methyl-4-quinolinecarboxamide.

CAS Registry No. 2348246-36-4; STN Entry Date: Jun. 28, 2019; N-(3,5-dichloro-4-hydroxyphenyl)-1-(1,1-dimethylethyl)-3-methyl-1H-Pyrazolo[3,4-b]pyridine-5-carboxamide.

CAS Registry No. 2401147-72-4; STN Entry Date: Jan. 7, 2020; N-(3,5-dichloro-4-hydroxyphenyl)-4-(1,1-dimethylethyl)-1H-Imidazole-5-carboxamide.

CAS Registry No. 2435276-99-4; STN Entry Date: Jun. 26, 2020; N-(3,5-dichloro-4-hydroxyphenyl)-1-(1,1-dimethylethyl)-5-methyl-1H-Pyrazole-3-carboxamide.

CAS Registry No. 847754-49-8; STN Entry Date: Apr. 1, 2005; 3,5-dichloro-4-hydroxy-N-[4-(1-methylpropyl)phenyl]-benzamide.

CAS Registry No. 880862-54-4; STN Entry Date: Apr. 18, 2006; 2-[(3,5-Dichloro-4-methoxybenzoyl)amino]-4,5,6,7-tetrahydro-N-[(tetrahydro-2-furanyl)methyl]benzo[b]thiophene-3-carboxamide.

CAS Registry No. 880862-64-6; STN Entry Date: Apr. 18, 2006; 2-[(3,5-Dichloro-4-methoxybenzoyl)amino]-5,6-dihydro-N-(2-phenylethyl)-4H-cyclopenta[b]thiophene-3-carboxamide.

CAS Registry No. 880864-93-7; STN Entry Date: Apr. 18, 2006; 2-[(4-Butoxy-3,5-dichlorobenzoyl)amino]-5,6-dihydro-N-(2-phenylethyl)-4H-cyclopenta[b]thiophene-3-carboxamide.

CAS Registry No. 880867-58-3; STN Entry Date: Apr. 18, 2006; 2-[[3,5-Dichloro-4-(hexyloxy)benzoyl]amino]-N-(3-ethoxypropyl)-4,5,6,7-tetrahydrobenzo[b]thiophene-3-carboxamide.

CAS Registry No. 880868-41-7; STN Entry Date: Apr. 18, 2006; 2-[[3,5-Dichloro-4-(heptyloxy)benzoyl]amino]-N-(3-ethoxypropyl)-5,6-dihydro-4H-cyclopenta[b]thiophene-3-carboxamide.

CAS Registry No. 882395-05-3; STN Entry Date: May 1, 2006; 2-[(3-Chloro-4-methoxybenzoyl)amino]-5,6-dihydro-N-(3-pyridinylmethyl)-4H-cyclopenta[b]thiophene-3-carboxamide.

CAS Registry No. 890962-86-4; STN Entry Date: Jul. 7, 2006; N-(3,5-Dichloro-4-hydroxyphenyl)-2,3-dihydro-2-(2-methylpropyl)-1,3-dioxo-1H-isoindole-5-carboxamide.

CAS Registry No. 926767-04-6; STN Entry Date: Mar. 18, 2007; 2-[(3-Chloro-4,5-dimethoxybenzoyl)amino]-4,5,6,7-tetrahydro-N-(phenylmethyl)benzo[b]thiophene-3-carboxamide.

Chao et al., Substituted isoquinolines and quinazolines as potential antiinflammatory agents. Synthesis and biological evaluation of inhibitors of tumor necrosis factor alpha. J Med Chem. 42(19):3860-3873 (1999).

Co-pending U.S. Appl. No. 18/479,578, inventors Anandan; Sampath Kumar et al., filed Oct. 2, 2023.

Co-pending U.S. Appl. No. 18/553,831, inventors Odingo; Joshua et al., filed Oct. 3, 2023.

Kim et al., Efficient solid-phase synthesis of 2,4-disubstituted 5-carbamoyl-thiazole derivatives using a traceless support. Tetrahedron 71(21):3367-3377 (2015).

Kralova et al. Inhibition of photosynthetic electron transport by some anilides of 2-alkylpyridine-4-carboxylic acids in spinach chloroplasts. Chemical Papers 52(1):52-55 (1998).

Lipnicka et al., New amides of 5-acylamino-3-methyl-4-isothiazolecarboxylic acid and their immunotropic activity. Arch Pharm (Weinheim) 338(7):322-328 (2005).

Machon et al., Synthesis and properties of 3-methyl-5-benzamidoisothiazole-4-carboxylic acid derivatives. Dissertationes Pharmaceuticae et Pharmacologicae 21(4):325-335 (1969).

PCT/US2021/042960 International Search Report and Written Opinion dated Sep. 20, 2021.

PCT/US2021/042999 International Search Report and Written Opinion dated Sep. 30, 2021.

PCT/US2021/058978 International Search Report and Written Opinion dated Dec. 23, 2021.

PCT/US2022/023350 International Search Report and Written Opinion dated Jun. 28, 2022.

PCT/US2022/023351 International Search Report and Written Opinion dated Jun. 15, 2022.

PCT/US2023/011520 International Search Report and Written Opinion dated Mar. 31, 2023.

Regiec et al., New isothiazole derivatives: synthesis, reactivity, physicochemical properties and pharmacological activity. Arch Pharm (Weinheim) 339(7):401-413 (2006).

Su et al., Comparative proteomic study reveals 17β-HSD13 as a pathogenic protein in nonalcoholic fatty liver disease. PNAS USA 11(31):11437-11442 (2014).

(56) References Cited

OTHER PUBLICATIONS

Thamm et al. Discovery of a Novel Potent and Selective HSD17B13 Inhibitor, BI-3231, a Well-Characterized Chemical Probe Available for Open Science. J Med Chem 66(4):2832-2850 (2023).
U.S. Appl. No. 18/315,138 Office Action dated Aug. 11, 2023.
U.S. Appl. No. 18/479,578 Office Action dated Jul. 2, 2024.

* cited by examiner

HYDROXYPYRIDINE HSD17B13 INHIBITORS AND USES THEREOF

CROSS-REFERENCE

This application claims the benefit of U.S. Provisional Application Ser. No. 63/170,852 filed Apr. 5, 2021 which is hereby incorporated by reference in its entirety.

BACKGROUND OF THE INVENTION

Nonalcoholic fatty liver diseases (NAFLDs) including NASH (nonalcoholic steatohepatitis) are considered to be hepatic manifestations of the metabolic syndrome and are characterized by the accumulation of triglycerides in the liver of patients without a history of excessive alcohol consumption. The majority of patients with NAFLD are obese or morbidly obese and have accompanying insulin resistance. The incidence of NAFLD/NASH has been rapidly increasing worldwide consistent with the increased prevalence of obesity, and it is currently the most common chronic liver disease.

NAFLD is classified into simple steatosis, in which only hepatic steatosis is observed, and NASH, in which intralobular inflammation and ballooning degeneration of hepatocytes is observed along with hepatic steatosis. The proportion of patients with NAFLD who have NASH is still not clear but might range from 20-40%. NASH is a progressive disease and may lead to liver cirrhosis and hepatocellular carcinoma. Twenty percent of NASH patients are reported to develop cirrhosis, and 30-40% of patients with NASH cirrhosis experience liver-related death. Recently, NASH has become the third most common indication for liver transplantation in the United States. Currently, the principal treatment for NAFLD/NASH is lifestyle modification by diet and exercise. However, pharmacological therapy is indispensable because obese patients with NAFLD often have difficulty maintaining improved lifestyles.

17β-Hydroxysteroid dehydrogenases (HSD17Bs) comprise a large family of 15 members some of which involved in sex hormone metabolism. Some HSD17Bs enzymes also play key roles in cholesterol and fatty acid metabolism. A recent study showed that hydroxysteroid 17β-dehydrogenase 13 (HSD17B13), an enzyme with unknown biological function, is a novel liver-specific lipid droplet (LD)-associated protein in mouse and humans. HSD17B13 expression is markedly upregulated in patients and mice with non-alcoholic fatty liver disease (NAFLD). Hepatic overexpression of HSD17B13 promotes lipid accumulation in the liver. HSD17B13 could also have potential as a biomarker of chronic liver disease, such as alcoholic liver disease (ALD), non-alcoholic fatty liver disease (NAFLD) (for example: steatosis, nonalcoholic steatohepatitis (NASH), NASH-fibrosis, or cirrhosis), steatohepatitis, and liver cancer.

SUMMARY OF THE INVENTION

Provided herein are methods, compounds, and compositions useful for reducing expression or activity of HSD17B13 in a subject in need thereof. Also, provided herein are methods, compounds, and compositions comprising HSD17B13 specific inhibitors, which can be useful in reducing the morbidity of HSD17B13-related diseases or conditions in a subject in need thereof. Such methods, compounds, and compositions can be useful, for example, to treat, prevent, delay or ameliorate liver disease, metabolic disease, or cardiovascular disease.

Disclosed herein is a compound of Formula (I), or a pharmaceutically acceptable salt, solvate, or stereoisomer thereof:

Formula (I)

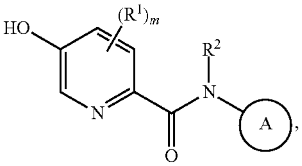

wherein:

each $R^1$ is independently hydrogen, deuterium, halogen, $—CN$, $—NO_2$, $—OH$, $—OR^a$, $—OC(=O)R^a$, $—OC(=O)OR^b$, $—OC(=O)NR^cR^d$, $—SH$, $—SR^a$, $—S(=O)R^a$, $—S(=O)_2R^a$, $—S(=O)_2NR^cR^d$, $—NR^cR^d$, $—NR^bC(=O)NR^cR^d$, $—NR^bC(=O)R^a$, $—NR^bC(=O)OR^b$, $—NHS(=O)_2R^a$, $—C(=O)R^a$, $—C(=O)OR^b$, $—C(=O)NR^cR^d$, $C_1$-$C_6$alkyl, $C_1$-$C_6$haloalkyl, $C_1$-$C_6$deuteroalkyl, $C_1$-$C_6$ hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

m is 1-3;

$R^2$ is hydrogen, $—C(=O)R^a$, $C_1$-$C_6$alkyl, $C_1$-$C_6$ haloalkyl, $C_1$-$C_6$deuteroalkyl, $C_1$-$C_6$hydroxyalkyl, $C_1$-$C_6$ aminoalkyl, $C_1$-$C_6$heteroalkyl, $C_2$-$C_6$alkenyl, $C_2$-$C_6$ alkynyl, cycloalkyl, heterocycloalkyl, aryl, or heteroaryl;

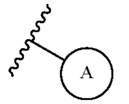 is 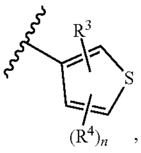, 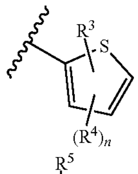, 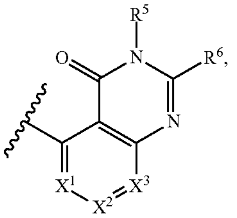, or 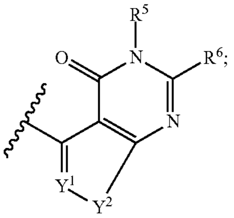

$R^3$ is hydrogen, deuterium, halogen, $—CN$, $—OH$, $—OR^{10}$, $—OC(=O)R^{10}$, $—OC(=O)OR^{11}$, $—OC(=O)NR^{12}R^{13}$, $—S(=O)R^{10}$, $—S(=O)_2R^{10}$, $—S(=O)_2NR^{12}R^{13}$, $—NR^{12}R^{13}$, $—NR^{11}C(=O)NR^{12}R^{13}$, $—NR^{11}C(=O)R^{10}$, $—NR^{11}C(=O)OR^{11}$, $—NR^{11}S(=O)_2R^{10}$, $—C(=O)R^{10}$, $—C(=O)OR^{11}$, $—C(=O)NR^{12}R^{13}$, $C_1$-$C_6$alkyl, $C_1$-$C_6$haloalkyl, $C_1$-$C_6$deuteroalkyl, $C_1$-$C_6$hydroxyalkyl, $C_1$-$C_6$ aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl)aryl, or ($C_1$-$C_6$alkyl)heteroaryl; wherein the alkyl, alkenyl, alkynyl, cycloalkyl, heterocycloalkyl, aryl, and heteroaryl is optionally and independently substituted with one or more $R^{3a}$;

each $R^{3a}$ is independently deuterium, halogen, $—CN$, $—OH$, $—OR^{10}$, $—OC(=O)R^{10}$, $—OC(=O)OR^{11}$, $—OC(=O)NR^{12}R^{13}$, $—S(=O)R^{10}$, $—S(=O)_2R^{10}$, —$S(=O)_2NR^{12}R^{13}$, —$NR^{12}R^{13}$, —$NR^{11}C(=O)NR^{12}R^{13}$, —$NR^{11}C(=O)R^{10}$, —$NR^{11}C(=O)OR^{11}$, —$NR^{11}S(=O)_2R^{10}$, —$C(=O)R^{10}$, —$C(=O)OR^{11}$, —$C(=O)NR^{12}R^{13}$, $C_1$-$C_6$alkyl, $C_1$-$C_6$haloalkyl, $C_1$-$C_6$deuteroalkyl, $C_1$-$C_6$hydroxyalkyl, $C_1$-$C_6$ aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl)aryl, or ($C_1$-$C_6$alkyl)heteroaryl;

or two $R^{3a}$ on the same atom form an oxo;

each $R^4$ is independently hydrogen, deuterium, halogen, —CN, —$NO_2$, —OH, —$OR^a$, —$OC(=O)R^a$, —$OC(=O)OR^b$, —$OC(=O)NR^cR^d$, —SH, —$SR^a$, —$S(=O)R^a$, —$S(=O)_2R^a$, —$S(=O)_2NR^cR^d$, —$NR^cR^d$, —$NR^bC(=O)NR^cR^d$, —$NR^bC(=O)R^a$, —$NR^bC(=O)OR^b$, —$NHS(=O)_2R^a$, —$C(=O)R^a$, —$C(=O)OR^b$, —$C(=O)NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^4$ are taken together to form a cycloalkyl, heterocycloalkyl, aryl, or heteroaryl; wherein the cycloalkyl, heterocycloalkyl, aryl, and heteroaryl is optionally substituted with one or more oxo, deuterium, halogen, —CN, —OH, —$OCH_3$, —$S(=O)CH_3$, —$S(=O)_2CH_3$, —$S(=O)_2NH_2$, —$S(=O)_2NHCH_3$, —$S(=O)_2N(CH_3)_2$, —$NH_2$, —$NHCH_3$, —$N(CH_3)_2$, —$C(=O)CH_3$, —$C(=O)OH$, —$C(=O)OCH_3$, $C_1$-$C_6$alkyl, $C_1$-$C_6$haloalkyl, $C_1$-$C_6$deuteroalkyl, $C_1$-$C_6$hydro- xyalkyl, or $C_1$-$C_6$aminoalkyl;

n is 1 or 2;

$R^5$ is hydrogen, deuterium, —$S(=O)R^{10}$, —$S(=O)_2R^{10}$, —$S(=O)_2NR^{12}R^{13}$, —$C(=O)R^{10}$, —$C(=O)OR^{11}$, —$C(=O)NR^{12}R^{13}$, —$C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl)aryl, or ($C_1$-$C_6$alkyl)heteroaryl; wherein the alkyl, alkenyl, alkynyl, cycloalkyl, heterocycloalkyl, aryl, and heteroaryl is optionally and independently substituted with one or more $R^{5a}$;

each $R^{5a}$ is independently deuterium, halogen, —CN, —OH, —$OR^{10}$, —$OC(=O)R^{10}$, —$OC(=O)OR^{11}$, —$OC(=O)NR^{12}R^{13}$, —$S(=O)R^{10}$, —$S(=O)_2R^{10}$, —$S(=O)_2NR^{12}R^{13}$, —$NR^{12}R^{13}$, —$NR^{11}C(=O)NR^{12}R^{13}$, —$NR^{11}C(=O)R^{10}$, —$NR^{11}C(=O)OR^{11}$, —$NR^{11}S(=O)_2R^{10}$, —$C(=O)R^{10}$, —$C(=O)OR^{11}$, —$C(=O)NR^{12}R^{13}$, $C_1$-$C_6$alkyl, $C_1$-$C_6$haloalkyl, $C_1$-$C_6$deuteroalkyl, $C_1$-$C_6$hydroxyalkyl, $C_1$-$C_6$ aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl)aryl, or ($C_1$-$C_6$alkyl)heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —$S(=O)CH_3$, —$S(=O)_2CH_3$, —$S(=O)_2NH_2$, —$S(=O)_2NHCH_3$, —$S(=O)_2N(CH_3)_2$, —$NH_2$, —$NHCH_3$, —$N(CH_3)_2$, —$C(=O)CH_3$, —$C(=O)OH$, —$C(=O)OCH_3$, $C_1$-$C_6$alkyl, $C_1$-$C_6$haloalkyl, $C_1$-$C_6$deuteroalkyl, $C_1$-$C_6$ hydroxyalkyl, $C_1$-$C_6$aminoalkyl, or $C_1$-$C_6$heteroalkyl;

or two $R^{5a}$ on the same atom form an oxo;

$R^6$ is hydrogen, deuterium, halogen, —CN, —$NO_2$, —OH, —$OR^a$, —$OC(=O)R^a$, —$OC(=O)OR^b$, —$OC(=O)NR^cR^d$, —SH, —$SR^a$, —$S(=O)R^a$, —$S(=O)_2R^a$, —$S(=O)_2NR^cR^d$, —$NR^cR^d$, —$NR^bC(=O)NR^cR^d$, —$NR^bC(=O)R^a$, —$NR^bC(=O)OR^b$, —$NHS(=O)_2R^a$, —$C(=O)R^a$, —$C(=O)OR^b$, —$C(=O)NR^cR^d$, $C_1$-$C_6$alkyl, $C_1$-$C_6$haloalkyl, $C_1$-$C_6$ deuteroalkyl, $C_1$-$C_6$hydroxyalkyl, $C_1$-$C_6$ aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

each $R^{10}$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$ aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl)aryl, or ($C_1$-$C_6$alkyl)heteroaryl; wherein the alkyl, alkenyl, alkynyl, cycloalkyl, heterocycloalkyl, aryl, and heteroaryl is optionally and independently substituted with one or more $R^{10a}$;

each $R^{11}$ is independently hydrogen, $C_1$-$C_6$alkyl, $C_1$-$C_6$haloalkyl, $C_1$-$C_6$deuteroalkyl, $C_1$-$C_6$ hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl)aryl, or ($C_1$-$C_6$alkyl)heteroaryl; wherein the alkyl, alkenyl, alkynyl, cycloalkyl, heterocycloalkyl, aryl, and heteroaryl is optionally and independently substituted with one or more $R^{11a}$;

each $R^{12}$ and $R^{13}$ are independently hydrogen, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_1$-$C_6$ heteroalkyl, $C_2$-$C_6$alkenyl, $C_2$-$C_6$alkynyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl)aryl, or ($C_1$-$C_6$alkyl)heteroaryl; wherein the alkyl, alkenyl, alkynyl, cycloalkyl, heterocycloalkyl, aryl, and heteroaryl is optionally and independently substituted with one or more $R^{12a}$;

or $R^{12}$ and $R^{13}$ are taken together with the atom to which they are attached to form a heterocycloalkyl optionally substituted with one or more $R^{12b}$;

each $R^{10a}$, $R^{11a}$, $R^{12a}$, or $R^{12b}$ are independently deuterium, halogen, —CN, —$NO_2$, —OH, —$OR^a$, —$OC(=O)R^a$, —$OC(=O)OR^b$, —$OC(=O)NR^cR^d$, —SH, —$SR^a$, —$S(=O)R^a$, —$S(=O)_2R^a$, —$S(=O)_2NR^cR^d$, —$NR^cR^d$, —$NR^bC(=O)NR^cR^d$, —$NR^bC(=O)R^a$, —$NR^bC(=O)OR^b$, —$NHS(=O)_2R^a$, —$C(=O)R^a$, —$C(=O)OR^b$, —$C(=O)NR^cR^d$, $C_1$-$C_6$alkyl, $C_1$-$C_6$haloalkyl, $C_1$-$C_6$deuteroalkyl, $C_1$-$C_6$ hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —$S(=O)CH_3$, —$S(=O)_2CH_3$, —$S(=O)_2NH_2$, —$S(=O)_2NHCH_3$, —$S(=O)_2N(CH_3)_2$, —$NH_2$, —$NHCH_3$, —$N(CH_3)_2$, —$C(=O)CH_3$, —$C(=O)OH$, —$C(=O)OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or two $R^{10a}$, or two $R^{11a}$, or two $R^{12a}$, or two $R^{12b}$ on the same atom are taken together to form an oxo;

$X^1$ is N or $CR^{X1}$;

$R^{X1}$ is hydrogen, deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

$X^2$ is N or $CR^{X2}$;

$R^{X2}$ is hydrogen, deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

$X^3$ is N or $CR^{X3}$;

$R^{X3}$ is hydrogen, deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

$Y^1$ is N or $CR^{Y1}$;

$R^{Y1}$ is hydrogen, deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

$Y^2$ is S, O, or $NR^{Y2}$;

$R^{Y2}$ is hydrogen, —C(═O)$R^a$, —C(═O)$OR^b$, —C(═O)$NR^cR^d$, $C_1$-$C_6$alkyl, $C_1$-$C_6$haloalkyl, $C_1$-$C_6$ deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, halogen, —CN, —OH, —$OCH_3$, —S(═O)$CH_3$, —S(═O)$_2CH_3$, —S(═O)$_2NH_2$, —S(═O)$_2NHCH_3$, —S(═O)$_2N(CH_3)_2$, —$NH_2$, —$NHCH_3$, —$N(CH_3)_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$ hydroxyalkyl, $C_1$-$C_6$aminoalkyl, $C_1$-$C_6$heteroalkyl;

each $R^b$ is independently hydrogen, $C_1$-$C_6$alkyl, $C_1$-$C_6$haloalkyl, $C_1$-$C_6$deuteroalkyl, $C_1$-$C_6$ hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, halogen, —CN, —OH, —$OCH_3$, —S(═O)$CH_3$, —S(═O)$_2CH_3$, —S(═O)$_2NH_2$, —S(═O)$_2NHCH_3$, —S(═O)$_2N(CH_3)_2$, —$NH_2$, —$NHCH_3$, —$N(CH_3)_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$ aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydro- xyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, halogen, —CN, —OH, —$OCH_3$, —S(═O)$CH_3$, —S(═O)$_2CH_3$, —S(═O)$_2NH_2$, —S(═O)$_2NHCH_3$, —S(═O)$_2N(CH_3)_2$, —$NH_2$, —$NHCH_3$, —$N(CH_3)_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$ aminoalkyl, or $C_1$-$C_6$heteroalkyl;

or $R^c$ and $R^d$ are taken together with the atom to which they are attached to form a heterocycloalkyl optionally substituted with one or more oxo, halogen, —CN, —OH, —$OCH_3$, —S(═O)$CH_3$, —S(═O)$_2CH_3$, —S(═O)$_2NH_2$, —S(═O)$_2NHCH_3$, —S(═O)$_2N(CH_3)_2$, —$NH_2$, —$NHCH_3$, —$N(CH_3)_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$ hydroxyalkyl, $C_1$-$C_6$aminoalkyl, or $C_1$-$C_6$heteroalkyl.

Disclosed herein is a compound of Formula (Ia), or a pharmaceutically acceptable salt, solvate, or stereoisomer thereof:

Formula (Ia)

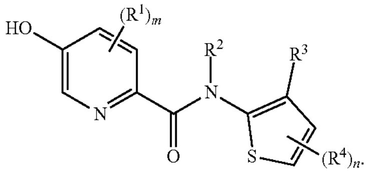

Disclosed herein is a compound of Formula (Ib), or a pharmaceutically acceptable salt, solvate, or stereoisomer thereof:

Formula (Ib)

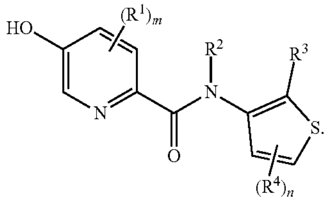

Disclosed herein is a compound of Formula (Ic), or a pharmaceutically acceptable salt, solvate, or stereoisomer thereof:

Formula (Ic)

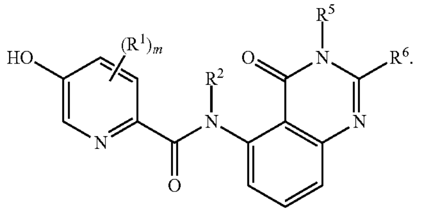

Disclosed herein is a compound of Formula (II), or a pharmaceutically acceptable salt, solvate, or stereoisomer thereof:

Formula (II)

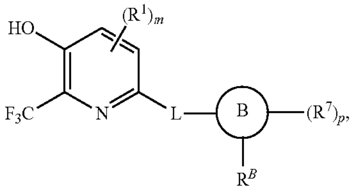

wherein:

each $R^1$ is independently hydrogen, deuterium, halogen, —CN, —$NO_2$, —OH, —$OR^a$, —OC(═O)$R^a$, —OC(═O)$OR^b$, —OC(═O)$NR^cR^d$, —SH, —$SR^a$, —S(═O)$R^a$, —S(═O)$_2R^a$, —S(═O)$_2NR^cR^d$, —$NR^cR^d$, —$NR^b$C(═O)$NR^cR^d$, —$NR^b$C(═O)$R^a$, —$NR^b$C(═O)$OR^b$, —NHS(═O)$_2R^a$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$ hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

m is 1 or 2;

L is $C_1$-$C_4$ alkylene, —O—, —S—, —$NR^2$—, —C(═O)$NR^2$—, —$NR^2$C(═O)—, —C(═O)O—, —OC(═O)—, —S(═O)$NR^2$—, —$NR^2$S(═O)—, —S(═O)$_2NR^2$—, —$NR^2$S(═O)$_2$—;

$R^2$ is hydrogen, —C(═O)$R^a$, $C_1$-$C_6$alkyl, $C_1$-$C_6$haloalkyl, $C_1$-$C_6$deuteroalkyl, $C_1$-$C_6$ hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

Ring B is cycloalkyl, heterocycloalkyl, aryl, or heteroaryl;

$R^B$ is hydrogen, deuterium, halogen, —CN, —OH, —$OR^{10}$, —OC(═O)$R^{10}$, —OC(═O)$OR^{11}$, —OC(═O)$NR^{12}R^{13}$, —S(═O)$R^{10}$, —S(═O)$_2R^{10}$, —S(═O)$_2NR^{12}R^{13}$, —$NR^{12}R^{13}$, —$NR^{11}$C(═O)$NR^{12}R^{13}$, —$NR^{11}$C(═O)$R^{10}$, —$NR^{11}$C(═O)$OR^{11}$, —$NR^{11}$S(═O)$_2R^{10}$, —C(═O)$R^{10}$, —C(═O)$OR^{11}$, —C(═O)$NR^{12}R^{13}$, $C_1$-$C_6$alkyl, $C_1$-$C_6$haloalkyl, $C_1$-$C_6$deuteroalkyl, $C_1$-$C_6$hydroxyalkyl, $C_1$-$C_6$ aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl)aryl, or ($C_1$-$C_6$alkyl)heteroaryl; wherein the alkyl, alkenyl, alkynyl, cycloalkyl, heterocycloalkyl, aryl, and heteroaryl is optionally and independently substituted with one or more $R^{Ba}$;

each $R^{Ba}$ is independently deuterium, halogen, —CN, —OH, —$OR^{10}$, —OC(═O)$R^{10}$, —OC(═O)$OR^{11}$, —OC(═O)$NR^{12}R^{13}$, —S(═O)$R^{10}$, —S(═O)$_2R^{10}$, —S(═O)$_2NR^{12}R^{13}$, —$NR^{12}R^{13}$, —$NR^{11}$C(═O)$NR^{12}R^{13}$, —$NR^{11}$C(═O)$R^{10}$, —$NR^{11}$C(═O)$OR^{11}$, —$NR^{11}$S(═O)$_2R^{10}$, —C(═O)$R^{10}$, —C(═O)$OR^{11}$, —C(═O)$NR^{12}R^{13}$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl)aryl, or ($C_1$-$C_6$alkyl)heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(═O)$CH_3$, —S(═O)$_2CH_3$, —S(═O)$_2NH_2$, —S(═O)$_2NHCH_3$, —S(═O)$_2N(CH_3)_2$, —$NH_2$, —$NHCH_3$, —$N(CH_3)_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or two $R^{Ba}$ on the same atom form an oxo;

each $R^7$ is independently hydrogen, deuterium, halogen, —CN, —$NO_2$, —OH, —$OR^a$, —OC(═O)$R^a$, —OC(═O)$OR^b$, —OC(═O)$NR^cR^d$, —SH, —$SR^a$, —S(═O)$R^a$, —S(═O)$_2R^a$, —S(═O)$_2NR^cR^d$, —$NR^cR^d$, —$NR^b$C(═O)$NR^cR^d$, —$NR^b$C(═O)$R^a$, —$NR^b$C(═O)$OR^b$, —NHS(═O)$_2R^a$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$ hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^7$ are taken together to form a cycloalkyl, heterocycloalkyl, aryl, or heteroaryl; wherein the cycloalkyl, heterocycloalkyl, aryl, and heteroaryl is optionally substituted with one or more oxo, deuterium, halogen, —CN, —OH, —$OCH_3$, —S(═O)$CH_3$, —S(═O)$_2CH_3$, —S(═O)$_2NH_2$, —S(═O)$_2NHCH_3$, —S(═O)$_2N(CH_3)_2$, —$NH_2$, —$NHCH_3$, —$N(CH_3)_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$ hydroxyalkyl, $C_1$-$C_6$aminoalkyl, or $C_1$-$C_6$heteroalkyl;

or two $R^7$ are taken together to form an oxo;

p is 1-4;

each $R^{10}$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$ aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl)aryl, or ($C_1$-$C_6$alkyl)heteroaryl; wherein the alkyl, alkenyl, alkynyl, cycloalkyl, heterocycloalkyl, aryl, and heteroaryl is optionally and independently substituted with one or more $R^{10a}$;

each $R^{11}$ is independently hydrogen, $C_1$-$C_6$alkyl, $C_1$-$C_6$haloalkyl, $C_1$-$C_6$deuteroalkyl, $C_1$-$C_6$ hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl)aryl, or ($C_1$-$C_6$alkyl)heteroaryl; wherein the alkyl, alkenyl, alkynyl, cycloalkyl, heterocycloalkyl, aryl, and heteroaryl is optionally and independently substituted with one or more $R^{11a}$;

each $R^{12}$ and $R^{13}$ are independently hydrogen, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl)aryl, or ($C_1$-$C_6$alkyl)heteroaryl; wherein the alkyl, alkenyl, alkynyl, cycloalkyl, heterocycloalkyl, aryl, and heteroaryl is optionally and independently substituted with one or more $R^{12a}$;

or $R^{12}$ and $R^{13}$ are taken together with the atom to which they are attached to form a heterocycloalkyl optionally substituted with one or more $R^{12b}$;

each $R^{10a}$, $R^{11a}$, $R^{12a}$, or $R^{12b}$ are independently deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^b$C(=O)$NR^cR^d$, —$NR^b$C(=O)$R^a$, —$NR^b$C(=O)$OR^b$, —NHS(=O)$_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$ hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$ hydroxyalkyl, $C_1$-$C_6$aminoalkyl, or $C_1$-$C_6$heteroalkyl;

or two $R^{10a}$, or two $R^{11a}$, or two $R^{12a}$, or two $R^{12b}$ on the same atom are taken together to form an oxo;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$a minoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one, two, or three deuterium, oxo, halogen, —CN, —OH, —OMe, —S(=O)Me, —S(=O)$_2$Me, —$NH_2$, —S(=O)$_2NH_2$, —C(=O)Me, —C(=O)OH, —C(=O)OMe, $C_1$-$C_6$alkyl, $C_1$-$C_6$ deuteroalkyl, $C_1$-$C_6$haloalkyl, $C_1$-$C_6$hydroxyalkyl, $C_1$-$C_6$aminoalkyl, or $C_1$-$C_6$heteroalkyl;

each $R^b$ is independently hydrogen, $C_1$-$C_6$alkyl, $C_1$-$C_6$haloalkyl, $C_1$-$C_6$deuteroalkyl, $C_1$-$C_6$ hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one, two, or three deuterium, oxo, halogen, —CN, —OH, —OMe, —S(=O)Me, —S(=O)$_2$Me, —$NH_2$, —S(=O)$_2NH_2$, —C(=O)Me, —C(=O)OH, —C(=O)OMe, $C_1$-$C_6$alkyl, $C_1$-$C_6$haloalkyl, $C_1$-$C_6$deuteroalkyl, $C_1$-$C_6$hydroxyalkyl, $C_1$-$C_6$ aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl, $C_1$-$C_6$ hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one, two, or three oxo, deuterium, halogen, —CN, —OH, —OMe, —S(=O)Me, —S(=O)$_2$Me, —$NH_2$, —S(=O)$_2NH_2$, —C(=O)Me, —C(=O)OH, —C(=O)OMe, $C_1$-$C_6$alkyl, $C_1$-$C_6$haloalkyl, $C_1$-$C_6$deuteroalkyl, $C_1$-$C_6$hydroxyalkyl, $C_1$-$C_6$ aminoalkyl, or $C_1$-$C_6$heteroalkyl;

or $R^c$ and $R^d$ are taken together with the atom to which they are attached to form a heterocycloalkyl optionally substituted with one, two, or three oxo, deuterium, halogen, —CN, —OH, —OMe, —S(=O)Me, —S(=O)$_2$Me, —$NH_2$, —S(=O)$_2NH_2$, —C(=O)Me, —C(=O)OH, —C(=O)OMe, $C_1$-$C_6$alkyl, $C_1$-$C_6$haloalkyl, $C_1$-$C_6$deuteroalkyl, $C_1$-$C_6$ hydroxyalkyl, $C_1$-$C_6$aminoalkyl, or $C_1$-$C_6$heteroalkyl; provided that the compound is not

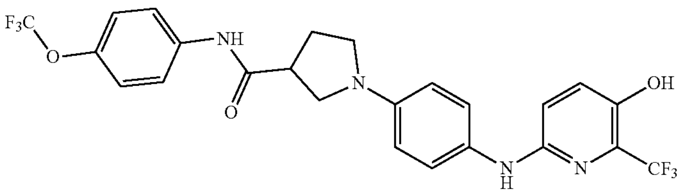

or

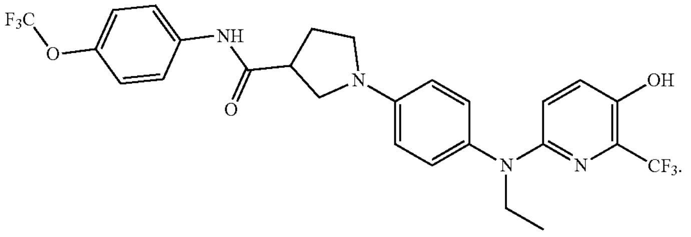

Also disclosed herein is a pharmaceutical composition comprising a compound disclosed herein, or a pharmaceutically acceptable salt, solvate, or stereoisomer thereof, and a pharmaceutically acceptable carrier.

Also disclosed herein is a method of treating a disease in a subject in need thereof, the method comprising administering a pharmaceutically effective amount of a compound disclosed herein, or a pharmaceutically acceptable salt, solvate, or stereoisomer thereof, or a pharmaceutical composition disclosed herein. In some embodiments of a method of treating a disease, the disease is a liver disease, a metabolic disease, or a cardiovascular disease. In some embodiments of a method of treating a disease, the disease is NAFLD. In some embodiments of a method of treating a disease, the disease is NASH. In some embodiments of a method of treating a disease, the disease is drug induced liver injury (DILI). In some embodiments of a method of treating a disease, the disease is associated with HSD17B13. In some embodiments of a method of treating a disease, the diseases is alcoholic liver disease. In some embodiments of a method of treating a disease, the disease is cirrhosis. In some embodiments of a method of treating a disease, the disease is decompensated portal hypertension.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "some embodiments" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"oxo" refers to =O.

"Carboxyl" refers to —COOH.

"Alkyl" refers to a straight-chain, or branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_{1-10}$alkyl. In some embodiments, the alkyl is a $C_{1-6}$alkyl. In some embodiments, the alkyl is a $C_{1-5}$alkyl. In some embodiments, the alkyl is a $C_{1-4}$alkyl. In some embodiments, the alkyl is a $C_{1-3}$alkyl. Unless stated otherwise specifically in the specification, an alkyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkyl is optionally substituted with oxo, halogen, —CN, —COOH, —COOMe, —OH, —OMe, —$NH_2$, or —$NO_2$. In some embodiments, the alkyl is optionally substituted with halogen, —CN, —OH, or —OMe. In some embodiments, the alkyl is optionally substituted with halogen.

"Alkenyl" refers to a straight-chain, or branched-chain hydrocarbon monoradical having one or more carbon-carbon double-bonds and having from two to about ten carbon atoms, more preferably two to about six carbon atoms. The group may be in either the cis or trans conformation about the double bond(s), and should be understood to include both isomers. Examples include, but are not limited to ethenyl (—CH=$CH_2$), 1-propenyl (—$CH_2$CH=$CH_2$), isopropenyl [—C($CH_3$)=$CH_2$], butenyl, 1,3-butadienyl and the like. Whenever it appears herein, a numerical range such as "$C_2$-$C_6$ alkenyl" or "$C_{2-6}$alkenyl", means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated. Unless stated otherwise specifically in the specification, an alkenyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkenyl is optionally substituted with oxo, halogen, —CN, —COOH, —COOMe, —OH, —OMe, —$NH_2$, or —$NO_2$. In some embodiments, the alkenyl is optionally substituted with halogen, —CN, —OH, or —OMe. In some embodiments, the alkenyl is optionally substituted with halogen.

"Alkynyl" refers to a straight-chain or branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "$C_2$-$C_6$ alkynyl" or "$C_{2-6}$alkynyl", means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated. Unless stated otherwise specifically in the specification, an alkynyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkynyl is optionally substituted with oxo, halogen, —CN, —COOH, COOMe, —OH, —OMe, $—NH_2$, or $—NO_2$. In some embodiments, the alkynyl is optionally substituted with halogen, —CN, —OH, or —OMe. In some embodiments, the alkynyl is optionally substituted with halogen.

"Alkylene" refers to a straight or branched divalent hydrocarbon chain. Unless stated otherwise specifically in the specification, an alkylene group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkylene is optionally substituted with oxo, halogen, —CN, —COOH, COOMe, —OH, —OMe, $—NH_2$, or $—NO_2$. In some embodiments, the alkylene is optionally substituted with halogen, —CN, —OH, or —OMe. In some embodiments, the alkylene is optionally substituted with halogen.

"Alkoxy" refers to a radical of the formula $—OR_a$ where $R_a$ is an alkyl radical as defined. Unless stated otherwise specifically in the specification, an alkoxy group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkoxy is optionally substituted with halogen, —CN, —COOH, COOMe, —OH, —OMe, $—NH_2$, or $—NO_2$. In some embodiments, the alkoxy is optionally substituted with halogen, —CN, —OH, or —OMe. In some embodiments, the alkoxy is optionally substituted with halogen.

"Aryl" refers to a radical derived from a hydrocarbon ring system comprising 6 to 30 carbon atoms and at least one aromatic ring. The aryl radical may be a monocyclic, bicyclic, tricyclic or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl (phenyl). Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl may be optionally substituted, for example, with halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the aryl is optionally substituted with halogen, methyl, ethyl, —CN, —COOH, COOMe, $—CF_3$, —OH, —OMe, $—NH_2$, or $—NO_2$. In some embodiments, the aryl is optionally substituted with halogen, methyl, ethyl, —CN, $—CF_3$, —OH, or —OMe. In some embodiments, the aryl is optionally substituted with halogen.

"Cycloalkyl" refers to a partially or fully saturated, monocyclic or polycyclic carbocyclic ring, which may include fused (when fused with an aryl or a heteroaryl ring, the cycloalkyl is bonded through a non-aromatic ring atom) or bridged ring systems. In some embodiments, the cycloalkyl is fully saturated. Representative cycloalkyls include, but are not limited to, cycloalkyls having from three to fifteen carbon atoms ($C_3$-$C_{15}$ cycloalkyl or $C_3$-$C_{15}$ cycloalkenyl), from three to ten carbon atoms ($C_3$-$C_{10}$ cycloalkyl or $C_3$-$C_{10}$ cycloalkenyl), from three to eight carbon atoms ($C_3$-$C_8$ cycloalkyl or $C_3$-$C_8$ cycloalkenyl), from three to six carbon atoms ($C_3$-$C_6$ cycloalkyl or $C_3$-$C_6$ cycloalkenyl), from three to five carbon atoms ($C_3$-$C_5$ cycloalkyl or $C_3$-$C_5$ cycloalkenyl), or three to four carbon atoms ($C_3$-$C_4$ cycloalkyl or $C_3$-$C_4$ cycloalkenyl). In some embodiments, the cycloalkyl is a 3- to 10-membered cycloalkyl or a 3- to 10-membered cycloalkenyl. In some embodiments, the cycloalkyl is a 3- to 6-membered cycloalkyl or a 3- to 6-membered cycloalkenyl. In some embodiments, the cycloalkyl is a 5- to 6-membered cycloalkyl or a 5- to 6-membered cycloalkenyl. Monocyclic cycloalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Partially saturated cycloalkyls include, for example cyclopentenyl, cyclohexenyl, cycloheptenyl, and cyclooctenyl. Unless stated otherwise specifically in the specification, a cycloalkyl is optionally substituted, for example, with oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, a cycloalkyl is optionally substituted with oxo, halogen, methyl, ethyl, —CN, —COOH, COOMe, $—CF_3$, —OH, —OMe, $—NH_2$, or $—NO_2$. In some embodiments, a cycloalkyl is optionally substituted with oxo, halogen, methyl, ethyl, —CN, $—CF_3$, —OH, or —OMe. In some embodiments, the cycloalkyl is optionally substituted with halogen.

"Halo" or "halogen" refers to bromo, chloro, fluoro or iodo. In some embodiments, halogen is fluoro or chloro. In some embodiments, halogen is fluoro.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Hydroxyalkyl" refers to an alkyl radical, as defined above, that is substituted by one or more hydroxyls. In some embodiments, the alkyl is substituted with one hydroxyl. In some embodiments, the alkyl is substituted with one, two, or three hydroxyls. Hydroxyalkyl include, for example, hydroxymethyl, hydroxyethyl, hydroxypropyl, hydroxybutyl, or hydroxypentyl. In some embodiments, the hydroxyalkyl is hydroxymethyl.

"Aminoalkyl" refers to an alkyl radical, as defined above, that is substituted by one or more amines. In some embodiments, the alkyl is substituted with one amine. In some embodiments, the alkyl is substituted with one, two, or three amines. Aminoalkyl include, for example, aminomethyl, aminoethyl, aminopropyl, aminobutyl, or aminopentyl. In some embodiments, the aminoalkyl is aminomethyl.

"Deuteroalkyl" refers to an alkyl radical, as defined above, that is substituted by one or more deuteriums. In some embodiments, the alkyl is substituted with one deuterium. In some embodiments, the alkyl is substituted with one, two, or three deuteriums. In some embodiments, the alkyl is substituted with one, two, three, four, five, or six deuteriums. Deuteroalkyl include, for example, $CD_3$, $CH_2D$, $CHD_2$, $CH_2CD_3$, $CD_2CD_3$, $CHDCD_3$, $CH_2CH_2D$, or $CH_2CHD_2$. In some embodiments, the deuteroalkyl is $CD_3$.

"Heteroalkyl" refers to an alkyl group in which one or more skeletal atoms of the alkyl are selected from an atom other than carbon, e.g., oxygen, nitrogen (e.g., —NH—, —N(alkyl)-), sulfur, phosphorus, or combinations thereof. A heteroalkyl is attached to the rest of the molecule at a carbon atom of the heteroalkyl. In one aspect, a heteroalkyl is a $C_1$-$C_6$ heteroalkyl wherein the heteroalkyl is comprised of 1 to 6 carbon atoms and one or more atoms other than carbon, e.g., oxygen, nitrogen (e.g. —NH—, —N(alkyl)-), sulfur, phosphorus, or combinations thereof wherein the heteroalkyl is attached to the rest of the molecule at a carbon atom of the heteroalkyl. Examples of such heteroalkyl are, for example, $—CH_2OCH_3$, $—CH_2CH_2OCH_3$, $—CH_2CH_2OCH_2CH_2OCH_3$, $—CH(CH_3)OCH_3$, $—CH_2NHCH_3$, $—CH_2N(CH_3)_2$, $—CH_2CH_2NHCH_3$, or $—CH_2CH_2N(CH_3)_2$. Unless stated otherwise specifically in the specification, a heteroalkyl is optionally substituted for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, $—CF_3$, —OH, —OMe, $—NH_2$, or $—NO_2$. In some embodiments, a heteroalkyl is optionally substituted with oxo, halogen, methyl, ethyl, —CN, $—CF_3$, —OH, or —OMe. In some embodiments, the heteroalkyl is optionally substituted with halogen.

"Heterocycloalkyl" refers to a 3- to 24-membered partially or fully saturated ring radical comprising 2 to 23 carbon atoms and from one to 8 heteroatoms selected from the group consisting of nitrogen, oxygen, phosphorous and sulfur. In some embodiments, the heterocycloalkyl is fully saturated. In some embodiments, the heterocycloalkyl comprises one to three heteroatoms selected from the group consisting of nitrogen, oxygen, and sulfur. In some embodiments, the heterocycloalkyl comprises one to three heteroatoms selected from the group consisting of nitrogen and oxygen. In some embodiments, the heterocycloalkyl comprises one to three nitrogens. In some embodiments, the heterocycloalkyl comprises one or two nitrogens. In some embodiments, the heterocycloalkyl comprises one nitrogen. In some embodiments, the heterocycloalkyl comprises one nitrogen and one oxygen. Unless stated otherwise specifically in the specification, the heterocycloalkyl radical may be a monocyclic, bicyclic, tricyclic or tetracyclic ring system, which may include fused (when fused with an aryl or a heteroaryl ring, the heterocycloalkyl is bonded through a non-aromatic ring atom) or bridged ring systems; and the nitrogen, carbon, or sulfur atoms in the heterocycloalkyl radical may be optionally oxidized; the nitrogen atom may be optionally quaternized. Representative heterocycloalkyls include, but are not limited to, heterocycloalkyls having from two to fifteen carbon atoms ($C_2$-$C_{15}$ heterocycloalkyl or $C_2$-$C_{15}$ heterocycloalkenyl), from two to ten carbon atoms ($C_2$-$C_{10}$ heterocycloalkyl or $C_2$-$C_{10}$ heterocycloalkenyl), from two to eight carbon atoms ($C_2$-$C_8$ heterocycloalkyl or $C_2$-$C_8$ heterocycloalkenyl), from two to seven carbon atoms ($C_2$-$C_7$ heterocycloalkyl or $C_2$-$C_7$ heterocycloalkenyl), from two to six carbon atoms ($C_2$-$C_6$ heterocycloalkyl or $C_2$-$C_7$ heterocycloalkenyl), from two to five carbon atoms ($C_2$-$C_5$ heterocycloalkyl or $C_2$-$C_5$ heterocycloalkenyl), or two to four carbon atoms ($C_2$-$C_4$ heterocycloalkyl or $C_2$-$C_4$ heterocycloalkenyl). Examples of such heterocycloalkyl radicals include, but are not limited to, aziridinyl, azetidinyl, oxetanyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). In some embodiments, the heterocycloalkyl is a 3- to 8-membered heterocycloalkyl. In some embodiments, the heterocycloalkyl is a 3- to 7-membered heterocycloalkyl. In some embodiments, the heterocycloalkyl is a 3- to 6-membered heterocycloalkyl. In some embodiments, the heterocycloalkyl is a 4- to 6-membered heterocycloalkyl. In some embodiments, the heterocycloalkyl is a 5- to 6-membered heterocycloalkyl. In some embodiments, the heterocycloalkyl is a 3- to 8-membered heterocycloalkenyl. In some embodiments, the heterocycloalkyl is a 3- to 7-membered heterocycloalkenyl. In some embodiments, the heterocycloalkyl is a 3- to 6-membered heterocycloalkenyl. In some embodiments, the heterocycloalkyl is a 4- to 6-membered heterocycloalkenyl. In some embodiments, the heterocycloalkyl is a 5- to 6-membered heterocycloalkenyl. Unless stated otherwise specifically in the specification, a heterocycloalkyl may be optionally substituted as described below, for example, with oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the heterocycloalkyl is optionally substituted with oxo, halogen, methyl, ethyl, —CN, —COOH, COOMe, $—CF_3$, —OH, —OMe, $—NH_2$, or $—NO_2$. In some embodiments, the heterocycloalkyl is optionally substituted with halogen, methyl, ethyl, —CN, $—CF_3$, —OH, or —OMe. In some embodiments, the heterocycloalkyl is optionally substituted with halogen.

"Heteroaryl" refers to a 5- to 14-membered ring system radical comprising one to thirteen carbon atoms, one to six heteroatoms selected from the group consisting of nitrogen, oxygen, phosphorous, and sulfur, and at least one aromatic ring. In some embodiments, the heteroaryl comprises one to three heteroatoms selected from the group consisting of nitrogen, oxygen, and sulfur. In some embodiments, the heteroaryl comprises one to three heteroatoms selected from the group consisting of nitrogen and oxygen. In some embodiments, the heteroaryl comprises one to three nitrogens. In some embodiments, the heteroaryl comprises one or two nitrogens. In some embodiments, the heteroaryl comprises one nitrogen. The heteroaryl radical may be a monocyclic, bicyclic, tricyclic or tetracyclic ring system, which may include fused (when fused with a cycloalkyl or heterocycloalkyl ring, the heteroaryl is bonded through an aromatic ring atom) or bridged ring systems; and the nitrogen, carbon or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. In some embodiments, the heteroaryl is a 6-membered heteroaryl. In some embodiments, the heteroaryl is a 5-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl may be optionally substituted, for example, with halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the heteroaryl is optionally substituted with halogen, methyl, ethyl, —CN, —COOH, COOMe, —$CF_3$, —OH, —OMe, —$NH_2$, or —$NO_2$. In some embodiments, the heteroaryl is optionally substituted with halogen, methyl, ethyl, —CN, —$CF_3$, —OH, or —OMe. In some embodiments, the heteroaryl is optionally substituted with halogen.

The term "optional" or "optionally" means that the subsequently described event or circumstance may or may not occur, and that the description includes instances where said event or circumstance occurs and instances in which it does not. For example. "optionally substituted alkyl" means either "alkyl" or "substituted alkyl" as defined above. Further, an optionally substituted group may be un-substituted (e.g., —$CH_2CH_3$), fully substituted (e.g., —$CF_2CF_3$), mono-substituted (e.g., —$CH_2CH_2F$) or substituted at a level anywhere in-between fully substituted and mono-substituted (e.g., —$CH_2CHF_2$, —$CH_2CF_3$, —$CF_2CH_3$, —$CFHCHF_2$, etc.). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons.

The term "one or more" when referring to an optional substituent means that the subject group is optionally substituted with one, two, three, or four. In some embodiments, the subject group is optionally substituted with one, two, or three substituents. In some embodiments, the subject group is optionally substituted with one or two substituents. In some embodiments, the subject group is optionally substituted with one substituent. In some embodiments, the subject group is optionally substituted with two substituents.

An "effective amount" or "therapeutically effective amount" refers to an amount of a compound administered to a mammalian subject, either as a single dose or as part of a series of doses, which is effective to produce a desired therapeutic effect.

"Treatment" of an individual (e.g. a mammal, such as a human) or a cell is any type of intervention used in an attempt to alter the natural course of the individual or cell. In some embodiments, treatment includes administration of a pharmaceutical composition, subsequent to the initiation of a pathologic event or contact with an etiologic agent and includes stabilization of the condition (e.g., condition does not worsen) or alleviation of the condition. In some embodiments, treatment also includes prophylactic treatment (e.g., administration of a composition described herein when an individual is suspected to be suffering from a liver disease, e.g., NAFLD).

"Synergy" or "synergize" refers to an effect of a combination that is greater than additive of the effects of each component alone at the same doses.

"HSD17B13" means hydroxysteroid 17-beta dehydrogenase 13 and refers to any nucleic acid of HSD17B13. For example, in some embodiments, HSD17B13 includes a DNA sequence encoding HSD17B13, an RNA sequence transcribed from DNA encoding HSD17B13 (including genomic DNA comprising introns and exons). HSD17B13 can also refer to any amino acid sequence of HSD17B13 (may include secondary or tertiary structures of the protein molecule), encoded by a DNA sequence and/or RNA sequence. The target may be referred to in either upper or lower case.

Compounds

Described herein are compounds, or a pharmaceutically acceptable salt, solvate, or stereoisomer thereof useful in the treatment of liver diseases. In some embodiments, the liver disease is NAFLD.

Disclosed herein is a compound of Formula (I), or a pharmaceutically acceptable salt, solvate, or stereoisomer thereof:

Formula (I)

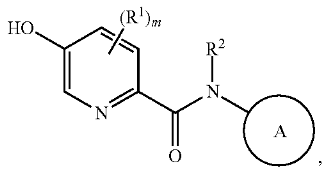

wherein:

each $R^1$ is independently hydrogen, deuterium, halogen, —CN, —$NO_2$, —OH, —$OR^a$, —$OC(=O)R^a$, —$OC(=O)OR^b$, —$OC(=O)NR^cR^d$, —SH, —$SR^a$, —$S(=O)R^a$, —$S(=O)_2R^a$, —$S(=O)_2NR^cR^d$, —$NR^cR^d$, —$NR^bC(=O)NR^cR^d$, —$NR^bC(=O)R^a$, —$NR^bC(=O)OR^b$, —$NHS(=O)_2R^a$, —$C(=O)R^a$, —$C(=O)OR^b$, —$C(=O)NR^cR^d$, $C_1$-$C_6$alkyl, $C_1$-$C_6$haloalkyl, $C_1$-$C_6$deuteroalkyl, $C_1$-$C_6$ hydroxyalkyl, $C_1$-$C_6$aminoalkyl, $C_1$-$C_6$heteroalkyl, $C_2$-$C_6$ alkenyl, $C_2$-$C_6$alkynyl, cycloalkyl, heterocycloalkyl, aryl, or heteroaryl;

m is 1-3;

$R^2$ is hydrogen, —$C(=O)R^a$, $C_1$-$C_6$alkyl, $C_1$-$C_6$ haloalkyl, $C_1$-$C_6$deuteroalkyl, $C_1$-$C_6$hydroxyalkyl, $C_1$-$C_6$ aminoalkyl, $C_1$-$C_6$heteroalkyl, $C_2$-$C_6$alkenyl, $C_2$-$C_6$ alkynyl, cycloalkyl, heterocycloalkyl, aryl, or heteroaryl;

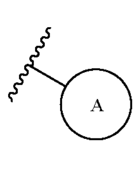 is 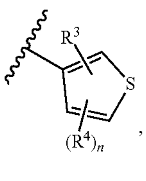 , 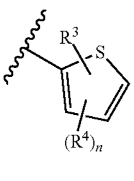 ,

-continued

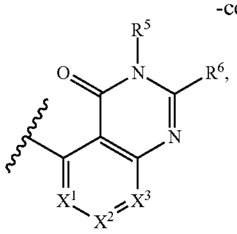 or 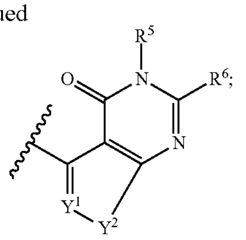

$R^3$ is hydrogen, deuterium, halogen, —CN, —OH, —$OR^{10}$, —OC(=O)$R^{10}$, —OC(=O)$OR^{11}$, —OC(=O)$NR^{12}R^{13}$, —S(=O)$R^{10}$, —$S(=O)_2R^{10}$, —$S(=O)_2NR^{12}R^{13}$, —$NR^{12}R^{13}$, —$NR^{11}C(=O)NR^{12}R^{13}$, —$NR^{11}C(=O)R^{10}$, —$NR^{11}C(=O)OR^{11}$, —$NR^{11}S(=O)_2R^{10}$, —C(=O)$R^{10}$, —C(=O)$OR^{11}$, —C(=O)$NR^{12}R^{13}$, $C_1$-$C_6$alkyl, $C_1$-$C_6$haloalkyl, $C_1$-$C_6$deuteroalkyl, $C_1$-$C_6$hydroxyalkyl, $C_1$-$C_6$ aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl)aryl, or ($C_1$-$C_6$alkyl)heteroaryl; wherein the alkyl, alkenyl, alkynyl, cycloalkyl, heterocycloalkyl, aryl, and heteroaryl is optionally and independently substituted with one or more $R^{3a}$;

each $R^{3a}$ is independently deuterium, halogen, —CN, —OH, —$OR^{10}$, —OC(=O)$R^{10}$, —OC(=O)$OR^{11}$, —OC(=O)$NR^{12}R^{13}$, —S(=O)$R^{10}$, —$S(=O)_2R^{10}$, —$S(=O)_2NR^{12}R^{13}$, —$NR^{12}R^{13}$, —$NR^{11}C(=O)NR^{12}R^{13}$, —$NR^{11}C(=O)R^{10}$, —$NR^{11}C(=O)OR^{11}$, —$NR^{11}S(=O)_2R^{10}$, —C(=O)$R^{10}$, —C(=O)$OR^{11}$, —C(=O)$NR^{12}R^{13}$, $C_1$-$C_6$alkyl, $C_1$-$C_6$haloalkyl, $C_1$-$C_6$deuteroalkyl, $C_1$-$C_6$hydroxyalkyl, $C_1$-$C_6$ aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl)aryl, or ($C_1$-$C_6$alkyl)heteroaryl;

or two $R^{3a}$ on the same atom form an oxo;

each $R^4$ is independently hydrogen, deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —$S(=O)_2R^a$, —$S(=O)_2NR^cR^d$, —$NR^cR^d$, —$NR^bC(=O)NR^cR^d$, —$NR^bC(=O)R^a$, —$NR^bC(=O)OR^b$, —$NHS(=O)_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^4$ are taken together to form a cycloalkyl, heterocycloalkyl, aryl, or heteroaryl; wherein the cycloalkyl, heterocycloalkyl, aryl, and heteroaryl is optionally substituted with one or more oxo, deuterium, halogen, —CN, —OH, —$OCH_3$, —S(=O)$CH_3$, —$S(=O)_2CH_3$, —$S(=O)_2NH_2$, —$S(=O)_2NHCH_3$, —$S(=O)_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, or $C_1$-$C_6$aminoalkyl;

n is 1 or 2;

$R^5$ is hydrogen, deuterium, —S(=O)$R^{10}$, —$S(=O)_2R^{10}$, —$S(=O)_2NR^{12}R^{13}$, —C(=O)$R^{10}$, —C(=O)$OR^{11}$, —C(=O)$NR^{12}R^{13}$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl)aryl, or ($C_1$-$C_6$alkyl)heteroaryl; wherein the alkyl, alkenyl, alkynyl, cycloalkyl, heterocycloalkyl, aryl, and heteroaryl is optionally and independently substituted with one or more $R^{5a}$;

each $R^{5a}$ is independently deuterium, halogen, —CN, —OH, —$OR^{10}$, —OC(=O)$R^{10}$, —OC(=O)$OR^{11}$, —OC(=O)$NR^{12}R^{13}$, —S(=O)$R^{10}$, —$S(=O)_2R^{10}$, —$S(=O)_2NR^{12}R^{13}$, —$NR^{12}R^{13}$, —$NR^{11}C(=O)NR^{12}R^{13}$, —$NR^{11}C(=O)R^{10}$, —$NR^{11}C(=O)OR^{11}$, —$NR^{11}S(=O)_2R^{10}$, —C(=O)$R^{10}$, —C(=O)$OR^{11}$, —C(=O)$NR^{12}R^{13}$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl)aryl, or ($C_1$-$C_6$alkyl)heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(=O)$CH_3$, —$S(=O)_2CH_3$, —$S(=O)_2NH_2$, —$S(=O)_2NHCH_3$, —$S(=O)_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or two $R^{5a}$ on the same atom form an oxo;

$R^6$ is hydrogen, deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —$S(=O)_2R^a$, —$S(=O)_2NR^cR^d$, —$NR^cR^d$, —$NR^bC(=O)NR^cR^d$, —$NR^bC(=O)R^a$, —$NR^bC(=O)OR^b$, —$NHS(=O)_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$ heteroalkyl, $C_2$-$C_6$alkenyl, $C_2$-$C_6$alkynyl, cycloalkyl, heterocycloalkyl, aryl, or heteroaryl;

each $R^{10}$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl)aryl, or ($C_1$-$C_6$alkyl)heteroaryl; wherein the alkyl, alkenyl, alkynyl, cycloalkyl, heterocycloalkyl, aryl, and heteroaryl is optionally and independently substituted with one or more $R^{10a}$;

each $R^{11}$ is independently hydrogen, $C_1$-$C_6$alkyl, $C_1$-$C_6$haloalkyl, $C_1$-$C_6$deuteroalkyl, $C_1$-$C_6$ hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl)aryl, or ($C_1$-$C_6$alkyl)heteroaryl; wherein the alkyl, alkenyl, alkynyl, cycloalkyl, heterocycloalkyl, aryl, and heteroaryl is optionally and independently substituted with one or more $R^{11a}$;

each $R^{12}$ and $R^{13}$ are independently hydrogen, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_1$-$C_6$ heteroalkyl, $C_2$-$C_6$alkenyl, $C_2$-$C_6$alkynyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl)aryl, or ($C_1$-$C_6$alkyl)heteroaryl; wherein the alkyl, alkenyl, alkynyl, cycloalkyl, heterocycloalkyl, aryl, and heteroaryl is optionally and independently substituted with one or more $R^{12a}$;

or R$^{12}$ and R$^{13}$ are taken together with the atom to which they are attached to form a heterocycloalkyl optionally substituted with one or more R$^{12b}$;

each R$^{10a}$, R$^{11a}$, R$^{12a}$, or R$^{12b}$ are independently deuterium, halogen, —CN, —NO$_2$, —OH, —OR$^a$, —OC(═O)R$^a$, —OC(═O)OR$^b$, —OC(═O)NR$^c$R$^d$, —SH, —SR$^a$, —S(═O)R$^a$, —S(═O)$_2$R$^a$, —S(═O)$_2$NR$^c$R$^d$, —NR$^c$R$^d$, —NR$^b$C(═O)NR$^c$R$^d$, —NR$^b$C(═O)R$^a$, —NR$^b$C(═O)OR$^b$, —NHS(═O)$_2$R$^a$, —C(═O)R$^a$, —C(═O)OR$^b$, —C(═O)NR$^c$R$^d$, $C_1$-$C_6$alkyl, $C_1$-$C_6$haloalkyl, $C_1$-$C_6$deuteroalkyl, $C_1$-$C_6$ hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OCH$_3$, —S(═O)CH$_3$, —S(═O)$_2$CH$_3$, —S(═O)$_2$NH$_2$, —S(═O)$_2$NHCH$_3$, —S(═O)$_2$N(CH$_3$)$_2$, —NH$_2$, —NHCH$_3$, —N(CH$_3$)$_2$, —C(═O)CH$_3$, —C(═O)OH, —C(═O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or two R$^{10a}$, or two R$^{11a}$, or two R$^{12a}$, or two R$^{12b}$ on the same atom are taken together to form an oxo;

X$^1$ is N or CR$^{X1}$;

R$^{X1}$ is hydrogen, deuterium, halogen, —CN, —OH, —OR$^a$, —NR$^c$R$^d$, —C(═O)R$^a$, —C(═O)OR$^b$, —C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

X$^2$ is N or CR$^{X2}$;

R$^{X2}$ is hydrogen, deuterium, halogen, —CN, —OH, —OR$^a$, —NR$^c$R$^d$, —C(═O)R$^a$, —C(═O)OR$^b$, —C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

X$^3$ is N or CR$^{X3}$;

R$^{X3}$ is hydrogen, deuterium, halogen, —CN, —OH, —OR$^a$, —NR$^c$R$^d$, —C(═O)R$^a$, —C(═O)OR$^b$, —C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

Y$^1$ is N or CR$^{Y1}$;

R$^{Y1}$ is hydrogen, deuterium, halogen, —CN, —OH, —OR$^a$, —NR$^c$R$^d$, —C(═O)R$^a$, —C(═O)OR$^b$, —C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

Y$^2$ is S, O, or NR$^{Y2}$;

R$^{Y2}$ is hydrogen, —C(═O)R$^a$, —C(═O)OR$^b$, —C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

each R$^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, halogen, —CN, —OH, —OCH$_3$, —S(═O)CH$_3$, —S(═O)$_2$CH$_3$, —S(═O)$_2$NH$_2$, —S(═O)$_2$NHCH$_3$, —S(═O)$_2$N(CH$_3$)$_2$, —NH$_2$, —NHCH$_3$, —N(CH$_3$)$_2$, —C(═O)CH$_3$, —C(═O)OH, —C(═O)OCH$_3$, $C_1$-$C_6$alkyl, $C_1$-$C_6$haloalkyl, $C_1$-$C_6$deuteroalkyl, $C_1$-$C_6$hyd- roxyalkyl, $C_1$-$C_6$aminoalkyl, $C_1$-$C_6$heteroalkyl;

each R$^b$ is independently hydrogen, $C_1$-$C_6$alkyl, $C_1$-$C_6$haloalkyl, $C_1$-$C_6$deuteroalkyl, $C_1$-$C_6$hydro- xyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, halogen, —CN, —OH, —OCH$_3$, —S(═O)CH$_3$, —S(═O)$_2$CH$_3$, —S(═O)$_2$NH$_2$, —S(═O)$_2$NHCH$_3$, —S(═O)$_2$N(CH$_3$)$_2$, —NH$_2$, —NHCH$_3$, —N(CH$_3$)$_2$, —C(═O)CH$_3$, —C(═O)OH, —C(═O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; and each R$^c$ and R$^d$ are independently hydrogen, $C_1$-$C_6$alkyl, $C_1$-$C_6$haloalkyl, $C_1$-$C_6$deuteroalkyl, $C_1$-$C_6$hydro- xyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, halogen, —CN, —OH, —OCH$_3$, —S(═O)CH$_3$, —S(═O), CH$_3$, —S(═O)$_2$NH$_2$, —S(═O)$_2$NHCH$_3$, —S(═O)$_2$N(CH$_3$)$_2$, —NH$_2$, —NHCH$_3$, —N(CH$_3$)$_2$, —C(═O)CH$_3$, —C(═O)OH, —C(═O)OCH$_3$, $C_1$-$C_6$alkyl, $C_1$-$C_6$haloalkyl, $C_1$-$C_6$deuteroalkyl, $C_1$-$C_6$ hydroxyalkyl, $C_1$-$C_6$aminoalkyl, or $C_1$-$C_6$heteroalkyl;

or R$^c$ and R$^d$ are taken together with the atom to which they are attached to form a heterocycloalkyl optionally substituted with one or more oxo, halogen, —CN, —OH, —OCH$_3$, —S(═O)CH$_3$, —S(═O)$_2$CH$_3$, —S(═O)$_2$NH$_2$, —S(═O)$_2$NHCH$_3$, —S(═O)$_2$N(CH$_3$)$_2$, —NH$_2$, —NHCH$_3$, —N(CH$_3$)$_2$, —C(═O)CH$_3$, —C(═O)OH, —C(═O)OCH$_3$, $C_1$-$C_6$alkyl, $C_1$-$C_6$haloalkyl, $C_1$-$C_6$deuteroalkyl, $C_1$-$C_6$ hydroxyalkyl, $C_1$-$C_6$aminoalkyl, or $C_1$-$C_6$heteroalkyl.

In some embodiments of a compound of Formula (I),

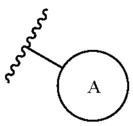 is 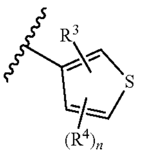 or 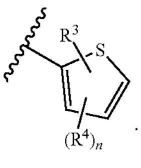.

In some embodiments of a compound of Formula (I),

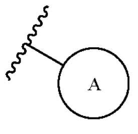

is

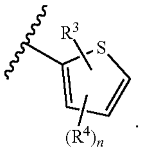

.

In some embodiments of a compound of Formula (I),

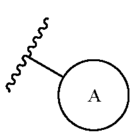

is

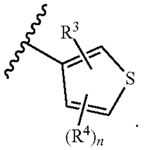

.

In some embodiments of a compound of Formula (I), the compound is of Formula (Ia):

Formula (Ia)

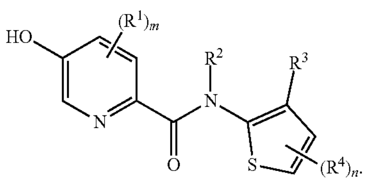

In some embodiments of a compound of Formula (I), the compound is of Formula (Ib):

Formula (Ib)

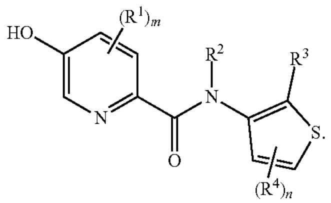

In some embodiments of a compound of Formula (I), (Ia), or (Ib), each $R^4$ is independently hydrogen, deuterium, halogen, —CN, —OH, —$OR^a$, —$NR^cR^d$, —$C(=O)R^a$, —$C(=O)OR^b$, —$C(=O)NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, cycloalkyl, heterocycloalkyl, aryl, or heteroaryl; or two $R^4$ are taken together to form a cycloalkyl, heterocycloalkyl, aryl, or heteroaryl; wherein the cycloalkyl, heterocycloalkyl, aryl, and heteroaryl is optionally substituted with one or more oxo, halogen, —CN, —OH, —$OCH_3$, —$S(=O)CH_3$, —$S(=O)_2CH_3$, —$S(=O)_2NH_2$, —$S(=O)_2NHCH_3$, —$S(=O)_2N(CH_3)_2$, —$NH_2$, —$NHCH_3$, —$N(CH_3)_2$, —$C(=O)CH_3$, —$C(=O)OH$, —$C(=O)OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl. In some embodiments of a compound of Formula (I), (Ia), or (Ib), each $R^4$ is independently hydrogen, deuterium, halogen, $C_1$-$C_6$alkyl, $C_1$-$C_6$haloalkyl, or $C_1$-$C_6$deuteroalkyl. In some embodiments of a compound of Formula (I), (Ia), or (Ib), each $R^4$ is independently hydrogen, deuterium, halogen, or $C_1$-$C_6$alkyl. In some embodiments of a compound of Formula (I), (Ia), or (Ib), each $R^4$ is independently hydrogen or halogen.

In some embodiments of a compound of Formula (I), (Ia), or (Ib), n is 1. In some embodiments of a compound of Formula (I), (Ia), or (Ib), n is 2.

In some embodiments of a compound of Formula (I), (Ia), or (Ib), $R^3$ is —$C(=O)R^{10}$, —$C(=O)OR^{11}$, or —$C(=O)NR^{12}R^{13}$. In some embodiments of a compound of Formula (I), (Ia), or (Ib), $R^3$ is —$C(=O)NR^{12}R^{13}$.

In some embodiments of a compound of Formula (I),

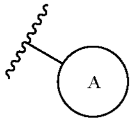

is

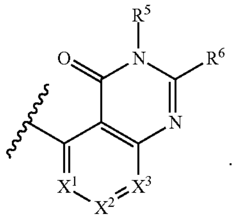

.

In some embodiments of a compound of Formula (I), $X^1$ is N. In some embodiments of a compound of Formula (I), $X^1$ is $CR^{X1}$. In some embodiments of a compound of Formula (I), $R^{X1}$ is hydrogen, deuterium, halogen, $C_1$-$C_6$alkyl, $C_1$-$C_6$haloalkyl, or $C_1$-$C_6$deuteroalkyl. In some embodiments of a compound of Formula (I), $R^{X1}$ is hydrogen.

In some embodiments of a compound of Formula (I), $X^2$ is N. In some embodiments of a compound of Formula (I), $X^2$ is $CR^{X2}$. In some embodiments of a compound of Formula (I), $R^{X2}$ is hydrogen, deuterium, halogen, $C_1$-$C_6$alkyl, $C_1$-$C_6$haloalkyl, or $C_1$-$C_6$deuteroalkyl. In some embodiments of a compound of Formula (I), $R^{X2}$ is hydrogen.

In some embodiments of a compound of Formula (I), $X^3$ is N. In some embodiments of a compound of Formula (I), $X^3$ is $CR^{X3}$. In some embodiments of a compound of Formula (I), $R^{X3}$ is hydrogen, deuterium, halogen, $C_1$-$C_6$alkyl, $C_1$-$C_6$haloalkyl, or $C_1$-$C_6$deuteroalkyl. In some embodiments of a compound of Formula (I), $R^{X3}$ is hydrogen.

In some embodiments of a compound of Formula (I), the compound is of Formula (Ic):

Formula (Ic)

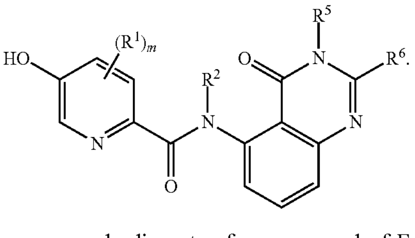

In some embodiments of a compound of Formula (I),

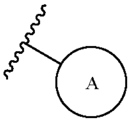

is

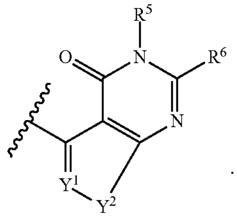

.

In some embodiments of a compound of Formula (I), $Y^1$ is N. In some embodiments of a compound of Formula (I), $Y^1$ is $CR^{Y1}$. In some embodiments of a compound of Formula (I), $R^{Y1}$ is hydrogen, deuterium, halogen, $C_1$-$C_6$alkyl, $C_1$-$C_6$haloalkyl, or $C_1$-$C_6$deuteroalkyl. In some embodiments of a compound of Formula (I), $R^{Y1}$ is hydrogen.

In some embodiments of a compound of Formula (I), $Y^2$ is S. In some embodiments of a compound of Formula (I), $Y^2$ is O. In some embodiments of a compound of Formula (I), $Y^2$ is $NR^{Y2}$. In some embodiments of a compound of Formula (I), $R^{Y2}$ is hydrogen or $C_1$-$C_6$alkyl. In some embodiments of a compound of Formula (I), $R^{Y2}$ is hydrogen.

In some embodiments of a compound of Formula (I) or (Ic), $R^6$ is hydrogen, deuterium, halogen, —CN, —OH, —$OR^a$, —OC(=O)$R^a$, —OC(=O)$OR^b$, —OC(=O)$NR^cR^d$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (I) or (Ic), $R^6$ is hydrogen, deuterium, halogen, —CN, —OH, —$OR^a$, —$NR^cR^d$, —C(=O)$R^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl. In some embodiments of a compound of Formula (I) or (Ic), $R^6$ is hydrogen or $C_1$-$C_6$alkyl.

In some embodiments of a compound of Formula (I) or (Ic), $R^5$ is $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl)aryl, or ($C_1$-$C_6$alkyl) heteroaryl; wherein the alkyl, cycloalkyl, heterocycloalkyl, aryl, and heteroaryl is optionally and independently substituted with one or more $R^{5a}$.

In some embodiments of a compound of Formula (I) or (Ic), $R^5$ is $C_1$-$C_6$alkyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl)aryl, or ($C_1$-$C_6$alkyl)heteroaryl; wherein the alkyl, cycloalkyl, heterocycloalkyl, aryl, and heteroaryl is optionally and independently substituted with one or more $R^{5a}$.

In some embodiments of a compound of Formula (I) or (Ic), $R^5$ is $C_1$-$C_6$alkyl, cycloalkyl, or ($C_1$-$C_6$alkyl)aryl; wherein the alkyl, cycloalkyl, and aryl is optionally and independently substituted with one or more $R^{5a}$.

In some embodiments of a compound of Formula (I) or (Ic), each $R^{5a}$ is independently deuterium, halogen, —OH, —$OR^{10}$, $C_1$-$C_6$alkyl, or $C_1$-$C_6$haloalkyl.

In some embodiments of a compound of Formula (I) or (Ia)-(Ic), each $R^{10}$ is independently $C_1$-$C_6$alkyl, $C_1$-$C_6$haloalkyl, $C_1$-$C_6$deuteroalkyl, $C_1$-$C_6$hydroxyalkyl, or $C_1$-$C_6$aminoalkyl; wherein the alkyl is optionally and independently substituted with one or more $R^{10a}$. In some embodiments of a compound of Formula (I) or (Ia)-(Ic), each $R^{10}$ is independently $C_1$-$C_6$alkyl.

In some embodiments of a compound of Formula (I) or (Ia)-(Ic), each $R^{11}$ is independently hydrogen, $C_1$-$C_6$alkyl, $C_1$-$C_6$haloalkyl, $C_1$-$C_6$deuteroalkyl, $C_1$-$C_6$hydroxyalkyl, or $C_1$-$C_6$aminoalkyl; wherein the alkyl is optionally and independently substituted with one or more $R^{11a}$. In some embodiments of a compound of Formula (I) or (Ia)-(Ic), each $R^{11}$ is independently hydrogen or $C_1$-$C_6$alkyl.

In some embodiments of a compound of Formula (I) or (Ia)-(Ic), each $R^{12}$ and $R^{13}$ are independently hydrogen, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl)aryl, or ($C_1$-$C_6$alkyl) heteroaryl; wherein the alkyl, cycloalkyl, heterocycloalkyl, aryl, and heteroaryl is optionally and independently substituted with one or more $R^{12a}$. In some embodiments of a compound of Formula (I) or (Ia)-(Ic), each $R^{12}$ and $R^{13}$ are independently hydrogen, $C_1$-$C_6$alkyl, $C_1$-$C_6$haloalkyl, cycloalkyl, ($C_1$-$C_6$alkyl)cycloalkyl, or ($C_1$-$C_6$alkyl)aryl; wherein the alkyl, cycloalkyl, and aryl is optionally and independently substituted with one or more $R^{12a}$.

In some embodiments of a compound of Formula (I) or (Ia)-(Ic), each $R^{12a}$ is independently deuterium, halogen, —OH, —$OR^a$, $C_1$-$C_6$alkyl, or $C_1$-$C_6$haloalkyl.

In some embodiments of a compound of Formula (I) or (Ia)-(Ic), $R^2$ is hydrogen.

In some embodiments of a compound of Formula (I) or (Ia)-(Ic), each $R^1$ is independently hydrogen, deuterium, halogen, —CN, —OH, —$OR^a$, —$NR^cR^d$, $C_1$-$C_6$alkyl, $C_1$-$C_6$haloalkyl, $C_1$-$C_6$deuteroalkyl, $C_1$-$C_6$hydroxyalkyl, or $C_1$-$C_6$aminoalkyl.

In some embodiments of a compound of Formula (I) or (Ia)-(Ic), each $R^1$ is independently hydrogen, halogen, or $C_1$-$C_6$haloalkyl.

In some embodiments of a compound of Formula (I) or (Ia)-(Ic), m is 1 or 2. In some embodiments of a compound of Formula (I) or (Ia)-(Ic), m is 1. In some embodiments of a compound of Formula (I) or (Ia)-(Ic), m is 2.

Disclosed herein is a compound of Formula (II), or a pharmaceutically acceptable salt, solvate, or stereoisomer thereof:

Formula (II)

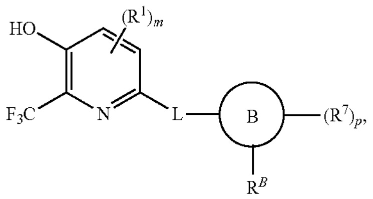

wherein:

each $R^1$ is independently hydrogen, deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^b$C(=O)$NR^cR^d$, —$NR^b$C(=O)$R^a$, —$NR^b$C(=O)$OR^b$, —NHS(=O)$_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

m is 1 or 2;

L is $C_1$-$C_4$ alkylene, —O—, —S—, —$NR^2$—, —C(=O)$NR^2$—, —$NR^2$C(=O)—, —C(=O)O—, —OC(=O)—, —S(=O)$NR^2$—, —$NR^2$S(=O)—, —S(=O)$_2NR^2$—, or —$NR^2$S(=O)$_2$—;

$R^2$ is hydrogen, —C(=O)$R^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

Ring B is cycloalkyl, heterocycloalkyl, aryl, or heteroaryl;

$R^B$ is hydrogen, deuterium, halogen, —CN, —OH, —$OR^{10}$, —OC(=O)$R^{10}$, —OC(=O)$OR^{11}$, —OC (=O)$NR^{12}R^{13}$, —S(=O)$R^{10}$, —S(=O)$_2R^{10}$, —S(=O)$_2NR^{12}R^{13}$, —$NR^{12}R^{13}$, —$NR^{11}$C(=O)$NR^{12}R^{13}$, —$NR^{11}$C(=O)$R^{10}$, —$NR^{11}$C(=O)$OR^{11}$, —$NR^{11}$S(=O)$_2R^{10}$, —C(=O)$R^{10}$, —C(=O)$OR^{11}$, —C(=O)$NR^{12}R^{13}$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl)aryl, or ($C_1$-$C_6$alkyl)heteroaryl; wherein the alkyl, alkenyl, alkynyl, cycloalkyl, heterocycloalkyl, aryl, and heteroaryl is optionally and independently substituted with one or more $R^{Ba}$;

each $R^{Ba}$ is independently deuterium, halogen, —CN, —OH, —$OR^{10}$, —OC(=O)$R^{10}$, —OC(=O)$OR^{11}$, —OC(=O)$NR^{12}R^{13}$, —S(=O)$R^{10}$, —S(=O)$_2R^{10}$, —S(=O)$_2NR^{12}R^{13}$, —$NR^{12}R^{13}$, —$NR^{11}$C(=O)$NR^{12}R^{13}$, —$NR^{11}$C(=O)$R^{10}$, —$NR^{11}$C(=O)$OR^{11}$, —$NR^{11}$S(=O)$_2R^{10}$, —C(=O)$R^{10}$, —C(=O)$OR^{11}$, —C(=O)$NR^{12}R^{13}$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl)aryl, or ($C_1$-$C_6$alkyl)heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or two $R^{Ba}$ on the same atom form an oxo;

each $R^7$ is independently hydrogen, deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^b$C(=O)$NR^cR^d$, —$NR^b$C(=O)$R^a$, —$NR^b$C(=O)$OR^b$, —NHS(=O)$_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^7$ are taken together to form a cycloalkyl, heterocycloalkyl, aryl, or heteroaryl; wherein the cycloalkyl, heterocycloalkyl, aryl, and heteroaryl is optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$ hydroxyalkyl, $C_1$-$C_6$aminoalkyl, or $C_1$-$C_6$heteroalkyl;

or two $R^7$ are taken together to form an oxo;

p is 1-4;

each $R^{10}$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$ aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl)aryl, or ($C_1$-$C_6$alkyl)heteroaryl; wherein the alkyl, alkenyl, alkynyl, cycloalkyl, heterocycloalkyl, aryl, and heteroaryl is optionally and independently substituted with one or more $R^{10a}$;

each $R^{11}$ is independently hydrogen, $C_1$-$C_6$alkyl, $C_1$-$C_6$haloalkyl, $C_1$-$C_6$deuteroalkyl, $C_1$-$C_6$hydr oxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl)aryl, or ($C_1$-$C_6$alkyl)heteroaryl; wherein the alkyl, alkenyl, alkynyl, cycloalkyl, heterocycloalkyl, aryl, and heteroaryl is optionally and independently substituted with one or more $R^{11a}$;

each $R^{12}$ and $R^{13}$ are independently hydrogen, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl)aryl, or ($C_1$-$C_6$alkyl)heteroaryl; wherein the alkyl, alkenyl, alkynyl, cycloalkyl, heterocycloalkyl, aryl, and heteroaryl is optionally and independently substituted with one or more $R^{12a}$;

or $R^{12}$ and $R^{13}$ are taken together with the atom to which they are attached to form a heterocycloalkyl optionally substituted with one or more $R^{12b}$;

each $R^{10a}$, $R^{11a}$, $R^{12a}$, or $R^{12b}$ are independently deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^b$C(=O)$NR^cR^d$, —$NR^b$C(=O)$R^a$, —$NR^b$C(=O)$OR^b$, —NHS(=O)$_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$ hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or two $R^{10a}$, or two $R^{11a}$, or two $R^{12a}$, or two $R^{12b}$ on the same atom are taken together to form an oxo;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one, two, or three deuterium, oxo, halogen, —CN, —OH, —OMe, —S(=O)Me, —S(=O)$_2$Me, —$NH_2$, —S(=O)$_2NH_2$, —C(=O)Me, —C(=O)OH, —C(=O)OMe, $C_1$-$C_6$alkyl, $C_1$-$C_6$deuteroalkyl, $C_1$-$C_6$haloalkyl, $C_1$-$C_6$hydro- xyalkyl, $C_1$-$C_6$aminoalkyl, or $C_1$-$C_6$heteroalkyl;

each $R^b$ is independently hydrogen, $C_1$-$C_6$alkyl, $C_1$-$C_6$haloalkyl, $C_1$-$C_6$deuteroalkyl, $C_1$-$C_6$hydro- xyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl): wherein each alkyl, alkenyl, alkynyl, cycloalkyl, heterocycloalkyl, aryl, and heteroaryl is independently optionally substituted with one, two, or three deuterium, oxo, halogen, —CN, —OH, —OMe, —S(═O)Me, —S(═O)$_2$Me, —NH$_2$, —S(═O)$_2$NH$_2$, —C(═O)Me, —C(═O)OH, —C(═O)OMe, $C_1$-$C_6$alkyl, $C_1$-$C_6$haloalkyl, $C_1$-$C_6$deuteroalkyl, $C_1$-$C_6$hydroxyalkyl, $C_1$-$C_6$ aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydro- xyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one, two, or three oxo, deuterium, halogen, —CN, —OH, —OMe, —S(═O)Me, —S(═O)$_2$Me, —NH$_2$, —S(═O)$_2$NH$_2$, —C(═O)Me, —C(═O)OH, —C(═O)OMe, $C_1$-$C_6$alkyl, $C_1$-$C_6$haloalkyl, $C_1$-$C_6$deuteroalkyl, $C_1$-$C_6$hydroxyalkyl, $C_1$-$C_6$ aminoalkyl, or $C_1$-$C_6$heteroalkyl;

or $R^c$ and $R^d$ are taken together with the atom to which they are attached to form a heterocycloalkyl optionally substituted with one, two, or three oxo, deuterium, halogen, —CN, —OH, —OMe, —S(═O)Me, —S(═O)$_2$Me, —NH$_2$, —S(═O)$_2$NH$_2$, —C(═O)Me, —C(═O)OH, —C(═O)OMe, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; provided that the compound is not

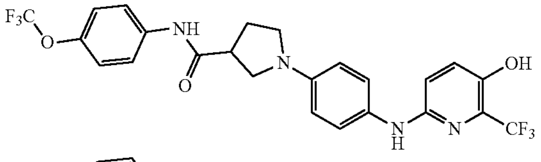

or

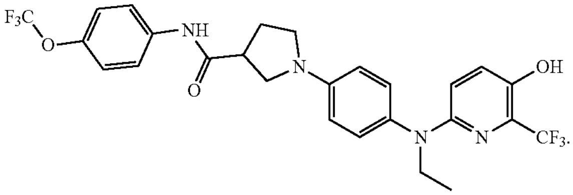

In some embodiments of a compound of Formula (II), L is $C_1$-$C_4$ alkylene, —O—, —S—, —C(═O)NR$^2$—, —NR$^2$C(═O)—, —C(═O)O—, —OC(═O)—, —S(═O)NR$^2$—, —NR$^2$S(═O)—, —S(═O)$_2$NR$^2$—, or —NR$^2$S(═O)$_2$—. In some embodiments of a compound of Formula (II), L is —C(═O)NR$^2$— or —NR$^2$C(═O)—.

In some embodiments of a compound of Formula (II), $R^2$ is hydrogen.

In some embodiments of a compound of Formula (II), Ring B is aryl or heteroaryl. In some embodiments of a compound of Formula (II), Ring B is phenyl. In some embodiments of a compound of Formula (II), Ring B is 5-membered heteroaryl. In some embodiments of a compound of Formula (II), Ring B is 6-membered heteroaryl. In some embodiments of a compound of Formula (II), Ring B is a bicyclic heteroaryl. In some embodiments of a compound of Formula (II), Ring B is a tricyclic heteroaryl.

In some embodiments of a compound of Formula (II),

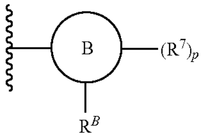

is

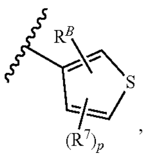

,

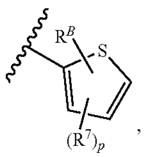

,

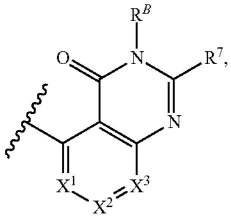

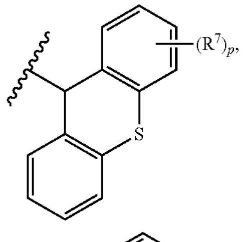

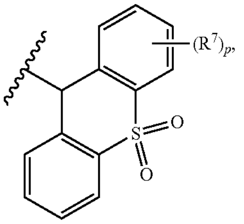

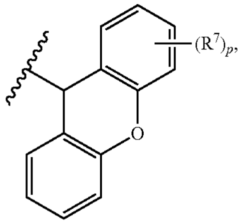

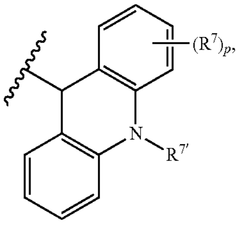

or

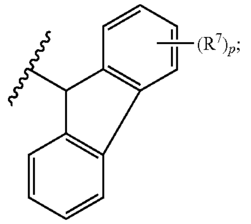

wherein $X^1$ is N or $CR^{X1}$;

$R^{X1}$ is hydrogen, deuterium, halogen, —CN, —OH, —OR$^a$, —NR$^c$R$^d$, —C(═O)R$^a$, —C(═O)OR$^b$, —C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$ aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

$X^2$ is N or $CR^{X2}$;

$R^{X2}$ is hydrogen, deuterium, halogen, —CN, —OH, —OR$^a$, —NR$^c$R$^d$, —C(═O)R$^a$, —C(═O)OR$^b$, —C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$ aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

$X^3$ is N or $CR^{X3}$;

$R^{X3}$ is hydrogen, deuterium, halogen, —CN, —OH, —OR$^a$, —NR$^c$R$^d$, —C(═O)R$^a$, —C(═O)OR$^b$, —C(═O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$ aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; and $R^{7'}$ is hydrogen or $C_1$-$C_6$alkyl.

In some embodiments of a compound of Formula (II),

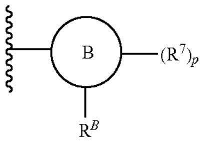

is

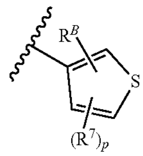

,

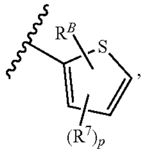

, or

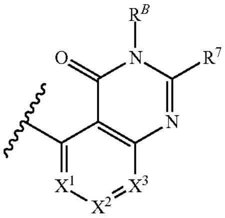

;

wherein $X^1$ is N or $CR^{X1}$;

$R^{X1}$ is hydrogen, deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

$X^2$ is N or $CR^{X2}$;

$R^{X2}$ is hydrogen, deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

$X^3$ is N or $CR^{X3}$; and $R^{X3}$ is hydrogen, deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl.

In some embodiments of a compound of Formula (II),

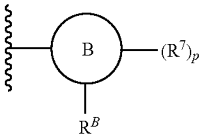

is

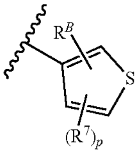

or

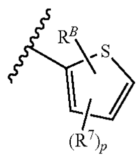

.

In some embodiments of a compound of Formula (II),

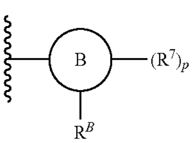

is

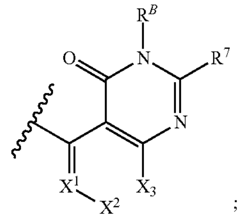

;

wherein $X^1$ is N or $CR^{X1}$;

$R^{X1}$ is hydrogen, deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

$X^2$ is N or $CR^{X2}$;

$R^{X2}$ is hydrogen, deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

$X^3$ is N or $CR^{X3}$; and $R^{X3}$ is hydrogen, deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl.

In some embodiments of a compound of Formula (II), $X^1$ is N. In some embodiments of a compound of Formula (II), $X^1$ is $CR^{X1}$. In some embodiments of a compound of Formula (II), $R^{X1}$ is hydrogen, deuterium, halogen, $C_1$-$C_6$alkyl, $C_1$-$C_6$haloalkyl, or $C_1$-$C_6$deuteroalkyl. In some embodiments of a compound of Formula (II), $R^{X1}$ is hydrogen.

In some embodiments of a compound of Formula (II), $X^2$ is N. In some embodiments of a compound of Formula (II), $X^2$ is $CR^{X2}$. In some embodiments of a compound of Formula (II), $R^{X2}$ is hydrogen, deuterium, halogen, $C_1$-$C_6$alkyl, $C_1$-$C_6$haloalkyl, or $C_1$-$C_6$deuteroalkyl. In some embodiments of a compound of Formula (II), $R^{X2}$ is hydrogen.

In some embodiments of a compound of Formula (II), $X^3$ is N. In some embodiments of a compound of Formula (II), $X^3$ is $CR^{X3}$. In some embodiments of a compound of Formula (II), $R^{X3}$ is hydrogen, deuterium, halogen, $C_1$-$C_6$alkyl, $C_1$-$C_6$haloalkyl, or $C_1$-$C_6$deuteroalkyl. In some embodiments of a compound of Formula (II), $R^{X3}$ is hydrogen.

In some embodiments of a compound of Formula (II), $R^B$ is —C(═O)$R^{10}$, —C(═O)$OR^{11}$, —C(═O)$NR^{12}R^{13}$, $C_1$-$C_6$alkyl, $C_1$-$C_6$haloalkyl, $C_1$-$C_6$deuteroalkyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl)aryl, or ($C_1$-$C_6$alkyl)heteroaryl; wherein the alkyl, cycloalkyl, heterocycloalkyl, aryl, and heteroaryl is optionally and independently substituted with one or more $R^{Ba}$. In some embodiments of a compound of Formula (II), $R^B$ is —C(═O)$NR^{12}R^{13}$, $C_1$-$C_6$alkyl, cycloalkyl, or ($C_1$-$C_6$alkyl)aryl; wherein the alkyl, cycloalkyl, and aryl is optionally and independently substituted with one or more $R^{Ba}$.

In some embodiments of a compound of Formula (II), each $R^{Ba}$ is independently deuterium, halogen, —CN, —OH, —$OR^{10}$, —$NR^{12}R^{13}$, $C_1$-$C_6$alkyl, $C_1$-$C_6$haloalkyl, $C_1$-$C_6$deuteroalkyl, $C_1$-$C_6$hydroxyalkyl, or $C_1$-$C_6$aminoalkyl.

In some embodiments of a compound of Formula (II), each $R^{12}$ and $R^{13}$ are independently hydrogen, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl)aryl, or ($C_1$-$C_6$alkyl)heteroaryl; wherein the alkyl, cycloalkyl, heterocycloalkyl, aryl, and heteroaryl is optionally and independently substituted with one or more $R^{12a}$. In some embodiments of a compound of Formula (II), each $R^{12}$ and $R^{13}$ are independently hydrogen, $C_1$-$C_6$alkyl, $C_1$-$C_6$haloalkyl, cycloalkyl, ($C_1$-$C_6$alkyl)cycloalkyl, or ($C_1$-$C_6$alkyl)aryl; wherein the alkyl, cycloalkyl, and aryl is optionally and independently substituted with one or more $R^{12a}$.

In some embodiments of a compound of Formula (II), each $R^{12a}$ is independently deuterium, halogen, —OH, —$OR^a$, $C_1$-$C_6$alkyl, or $C_1$-$C_6$haloalkyl.

In some embodiments of a compound of Formula (II), each $R^1$ is independently hydrogen, deuterium, halogen, —CN, —OH, —$OR^a$, —$NR^cR^d$, $C_1$-$C_6$alkyl, $C_1$-$C_6$haloalkyl, $C_1$-$C_6$deuteroalkyl, $C_1$-$C_6$hydroxyalkyl, or $C_1$-$C_6$aminoalkyl. In some embodiments of a compound of Formula (II), each $R^1$ is independently hydrogen, halogen, or $C_1$-$C_6$haloalkyl.

In some embodiments of a compound of Formula (II), m is 1. In some embodiments of a compound of Formula (II), m is 1 or 2.

In some embodiments of a compound of Formula (II), each $R^7$ is independently hydrogen, deuterium, halogen, —OH, $C_1$-$C_6$alkyl, $C_1$-$C_6$haloalkyl, or $C_1$-$C_6$deuteroalkyl; or two $R^7$ are taken together to form an oxo. In some embodiments of a compound of Formula (II), each $R^7$ is independently hydrogen, deuterium, halogen, —OH, or $C_1$-$C_6$alkyl; or two $R^7$ are taken together to form an oxo.

In some embodiments of a compound of Formula (II), p is 1. In some embodiments of a compound of Formula (II), p is 2.

Also disclosed herein is a compound of Formula (III), or a pharmaceutically acceptable salt, solvate, or stereoisomer thereof:

Formula (III)

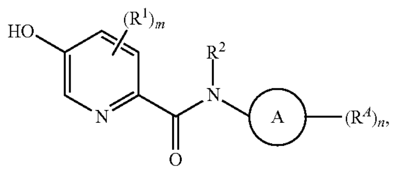

wherein:

each $R^1$ is independently hydrogen, deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^b$C(=O)$NR^cR^d$, —$NR^b$C(=O)$R^a$, —$NR^b$C(=O)$OR^b$, —NHS(=O)$_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

m is 1-3;

$R^2$ is hydrogen, —C(=O)$R^a$, $C_1$-$C_6$alkyl, $C_1$-$C_6$ haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

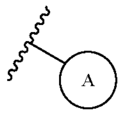

is a tricyclic ring;

each $R^A$ is independently hydrogen, deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^b$C(=O)$NR^cR^d$, —$NR^b$C(=O)$R^a$, —$NR^b$C(=O)$OR^b$, —NHS(=O)$_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^A$ on the same atom are taken together to form an oxo;

n is 1-4;

each $R^b$ is independently hydrogen, $C_1$-$C_6$alkyl, $C_1$-$C_6$haloalkyl, $C_1$-$C_6$deuteroalkyl, $C_1$-$C_6$ hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$ aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl, $C_1$-$C_6$ hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$ aminoalkyl, or $C_1$-$C_6$heteroalkyl;

or $R^c$ and $R^d$ are taken together with the atom to which they are attached to form a heterocycloalkyl optionally substituted with one or more oxo, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$ hydroxyalkyl, $C_1$-$C_6$aminoalkyl, or $C_1$-$C_6$heteroalkyl.

In some embodiments of a compound of Formula (III),

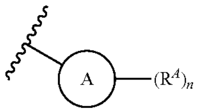 is 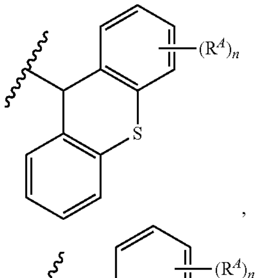, 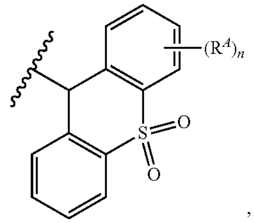, 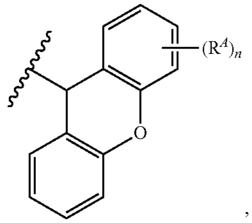, 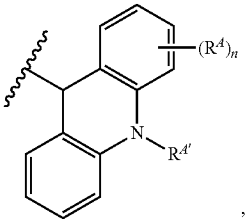, or 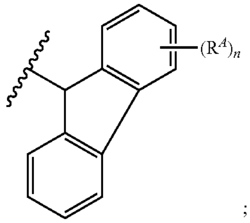;

wherein $R^{A'}$ is hydrogen or $C_1$-$C_6$alkyl.

In some embodiments of a compound of Formula (III), each $R^A$ is independently hydrogen, deuterium, halogen, —CN, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, heterocycloalkyl, aryl, or heteroaryl; or two $R^A$ on the same atom are taken together to form an oxo. In some embodiments of a compound of Formula (III), each $R^A$ is independently hydrogen, deuterium, halogen, —CN, —OH, —$OR^a$, —$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl; or two $R^A$ on the same atom are taken together to form an oxo. In some embodiments of a compound of Formula (III), each $R^A$ is independently hydrogen, deuterium, halogen, —CN, —OH, —$OR^a$, —$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl; or two $R^A$ on the same atom are taken together to form an oxo. In some embodiments of a compound of Formula (III), each $R^A$ is independently hydrogen, deuterium, halogen, —CN, —OH, —$OR^a$, —$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl. In some embodiments of a compound of Formula (III), each $R^A$ is independently hydrogen, deuterium, halogen, —CN, $C_1$-$C_6$alkyl, $C_1$-$C_6$haloalkyl, or $C_1$-$C_6$deuteroalkyl.

In some embodiments of a compound of Formula (III), n is 1 or 2. In some embodiments of a compound of Formula (III), n is 2 or 3. In some embodiments of a compound of Formula (III), n is 2.

In some embodiments of a compound of Formula (III), $R^2$ is hydrogen.

In some embodiments of a compound of Formula (III), each $R^1$ is independently hydrogen, deuterium, halogen, —CN, —OH, —$OR^a$, —$NR^cR^d$, $C_1$-$C_6$alkyl, $C_1$-$C_6$haloalkyl, $C_1$-$C_6$deuteroalkyl, $C_1$-$C_6$hydroxyalkyl, or $C_1$-$C_6$aminoalkyl.

In some embodiments of a compound of Formula (III), each $R^1$ is independently hydrogen, halogen, or $C_1$-$C_6$haloalkyl.

In some embodiments of a compound of Formula (III), m is 1 or 2. In some embodiments of a compound of Formula (III), m is 1. In some embodiments of a compound of Formula (III), m is 2.

In some embodiments of a compound disclosed herein, each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, halogen, —CN, —OH, —$OCH_3$, —S(=O)$CH_3$, —$S(=O)_2CH_3$, —$S(=O)_2NH_2$, —$S(=O)_2NHCH_3$, —$S(=O)_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl. In some embodiments of a compound disclosed herein, each $R^a$ is independently $C_1$-$C_6$alkyl, $C_1$-$C_6$haloalkyl, cycloalkyl, or heterocycloalkyl; wherein each alkyl, cycloalkyl, and heterocycloalkyl is independently optionally substituted with one or more oxo, halogen, —CN, —OH, —$OCH_3$, —S(=O)$CH_3$, —$S(=O)_2CH_3$, —$S(=O)_2NH_2$, —$S(=O)_2NHCH_3$, —$S(=O)_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl. In some embodiments of a compound disclosed herein, each $R^a$ is independently $C_1$-$C_6$alkyl, $C_1$-$C_6$haloalkyl, cycloalkyl, or heterocycloalkyl. In some embodiments of a compound disclosed herein, each $R^a$ is independently $C_1$-$C_6$alkyl or $C_1$-$C_6$haloalkyl. In some embodiments of a compound disclosed herein, each $R^a$ is independently $C_1$-$C_6$alkyl.

In some embodiments of a compound disclosed herein, each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, halogen, —CN, —OH, —$OCH_3$, —S(=O)$CH_3$, —$S(=O)_2CH_3$, —$S(=O)_2NH_2$, —$S(=O)_2NHCH_3$, —$S(=O)_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl. In some embodiments of a compound disclosed herein, each $R^b$ is independently hydrogen, $C_1$-$C_6$alkyl, $C_1$-$C_6$haloalkyl, cycloalkyl, or heterocycloalkyl; wherein each alkyl, cycloalkyl, and heterocycloalkyl is independently optionally substituted with one or more oxo, halogen, —CN, —OH, —$OCH_3$, —S(=O)$CH_3$, —$S(=O)_2CH_3$, —$S(=O)_2NH_2$, —$S(=O)_2NHCH_3$, —$S(=O)_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl. In some embodiments of a compound disclosed herein, each $R^b$ is independently hydrogen, $C_1$-$C_6$alkyl, $C_1$-$C_6$haloalkyl, cycloalkyl, or heterocycloalkyl. In some embodiments of a compound disclosed herein, each $R^b$ is independently hydrogen, $C_1$-$C_6$alkyl, or $C_1$-$C_6$haloalkyl. In some embodiments of a compound disclosed herein, each $R^b$ is independently hydrogen or $C_1$-$C_6$alkyl.

In some embodiments of a compound disclosed herein, each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, halogen, —CN, —OH, —$OCH_3$, —S(═O)$CH_3$, —S(═O)$_2CH_3$, —S(═O)$_2NH_2$, —S(═O)$_2NHCH_3$, —S(═O)$_2N(CH_3)_2$, —$NH_2$, —$NHCH_3$, —$N(CH_3)_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl. In some embodiments of a compound disclosed herein, each $R^c$ and $R^d$ are independently hydrogen, $C_1$-$C_6$alkyl, $C_1$-$C_6$haloalkyl, cycloalkyl, or heterocycloalkyl; wherein each alkyl, cycloalkyl, and heterocycloalkyl is independently optionally substituted with one or more oxo, halogen, —CN, —OH, —$OCH_3$, —S(═O)$CH_3$, —S(═O)$_2CH_3$, —S(═O)$_2NH_2$, —S(═O)$_2NHCH_3$, —S(═O)$_2N(CH_3)_2$, —$NH_2$, —$NHCH_3$, —$N(CH_3)_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl. In some embodiments of a compound disclosed herein, each $R^c$ and $R^d$ are independently hydrogen, $C_1$-$C_6$alkyl, $C_1$-$C_6$haloalkyl, cycloalkyl, or heterocycloalkyl. In some embodiments of a compound disclosed herein, each $R^c$ and $R^d$ are independently hydrogen, $C_1$-$C_6$alkyl, or $C_1$-$C_6$haloalkyl. In some embodiments of a compound disclosed herein, each $R^c$ and $R^d$ are independently hydrogen or $C_1$-$C_6$alkyl.

In some embodiments of a compound disclosed herein, $R^c$ and $R^d$ are taken together with the atom to which they are attached to form a heterocycloalkyl optionally substituted with one or more oxo, halogen, —CN, —OH, —$OCH_3$, —$NH_2$, —$NHCH_3$, —$N(CH_3)_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl.

In some embodiments of a compound disclosed herein, each $R^3$, $R^5$, $R^{5a}$, $R^{10}$, $R^{11}$, $R^{12}$, $R^{13}$, $R^{10a}$, $R^{11a}$, $R^{12a}$, $R^{12b}$, $R^B$, $R^{Ba}$, $R^a$, $R^b$, $R^c$, $R^d$, the heterocycloalkyl formed when $R^{12}$ and $R^{13}$ are taken together, and the heterocycloalkyl formed when $R^c$ and $R^d$ are taken together is independently substituted with one, two, three, or four substituents as defined herein. In some embodiments of a compound disclosed herein, each $R^3$, $R^5$, $R^{5a}$, $R^{10}$, $R^{11}$, $R^{12}$, $R^{13}$, $R^{10a}$, $R^{11a}$, $R^{12a}$, $R^{12b}$, $R^B$, $R^{Ba}$, $R^a$, $R^b$, $R^c$, $R^d$, the heterocycloalkyl formed when $R^{12}$ and $R^{13}$ are taken together, and the heterocycloalkyl formed when $R^c$ and $R^d$ are taken together is independently substituted with one, two, or three substituents as defined herein. In some embodiments of a compound disclosed herein, each $R^3$, $R^5$, $R^{5a}$, $R^{10}$, $R^{11}$, $R^{12}$, $R^{13}$, $R^{10a}$, $R^{11a}$, $R^{12a}$, $R^{12b}$, $R^B$, $R^{Ba}$, $R^a$, $R^b$, $R^c$, $R^d$, the heterocycloalkyl formed when $R^{12}$ and $R^{13}$ are taken together, and the heterocycloalkyl formed when $R^c$ and $R^d$ are taken together is independently substituted with one or two substituents as defined herein. In some embodiments of a compound disclosed herein, each $R^3$, $R^5$, $R^{5a}$, $R^{10}$, $R^{11}$, $R^{12}$, $R^{13}$, $R^{10a}$, $R^{11a}$, $R^{12a}$, $R^{12b}$, $R^B$, $R^{Ba}$, $R^a$, $R^b$, $R^c$, $R^d$, the heterocycloalkyl formed when $R^{12}$ and $R^{13}$ are taken together, and the heterocycloalkyl formed when $R^c$ and $R^d$ are taken together is independently substituted with one substituent as defined herein.

Any combination of the groups described above for the various variables is contemplated herein. Throughout the specification, groups and substituents thereof are chosen by one skilled in the field to provide stable moieties and compounds.

Described herein is a compound of Formula (I), (Ia)-(Ic), (II), or (III), or a pharmaceutically acceptable salt, solvate, or stereoisomer thereof, selected from a compound in Table 1.

TABLE 1

| Exemplary compounds | | |
|---|---|---|
| Ex. | Structure | Name |
| 1 | 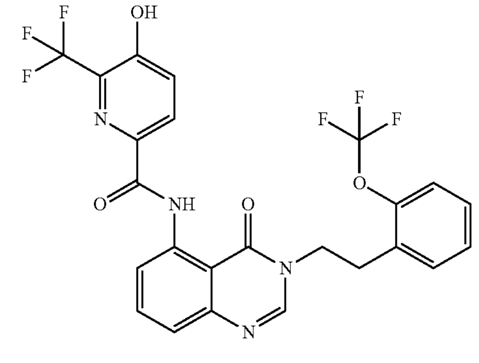 [SMILES: O=C(Nc1cccc2ncn(CCc3ccccc3OC(F)(F)F)c(=O)c12)c1ccc(O)c(C(F)(F)F)n1] | 5-hydroxy-N-(4-oxo-3-(2-(trifluoromethoxy)phenethyl)-3,4-dihydroquinazolin-5-yl)-6-(trifluoromethyl)picolinamide |
| 2 | 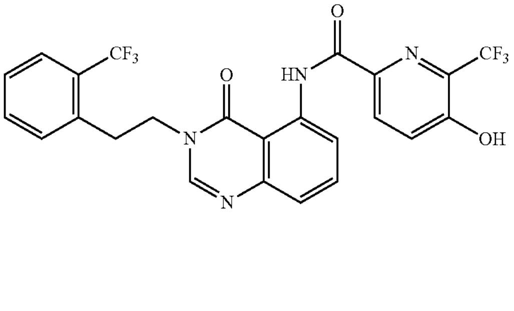 [SMILES: O=C(Nc1cccc2ncn(CCc3ccccc3C(F)(F)F)c(=O)c12)c1ccc(O)c(C(F)(F)F)n1] | 5-hydroxy-N-(4-oxo-3-(2-(trifluoromethyl)phenethyl)-3,4-dihydroquinazolin-5-yl)-6-(trifluoromethyl)picolinamide |

TABLE 1-continued

| Exemplary compounds | | |
|---|---|---|
| Ex. | Structure | Name |
| 3 | 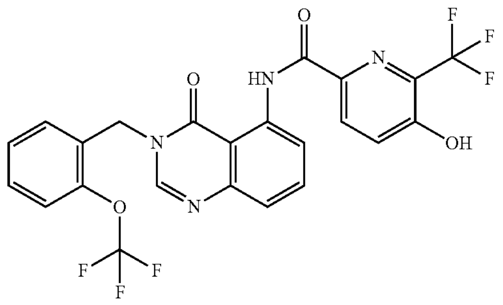 [SMILES: O=C(Nc1cccc2ncn(Cc3ccccc3OC(F)(F)F)c(=O)c12)c1ccc(O)c(C(F)(F)F)n1] | 5-hydroxy-N-(4-oxo-3-{[2-(trifluoromethoxy)phenyl] methyl}-3,4-dihydroquinazolin-5-yl)-6-(trifluoromethyl) pyridine-2-carboxamide |
| 4 | 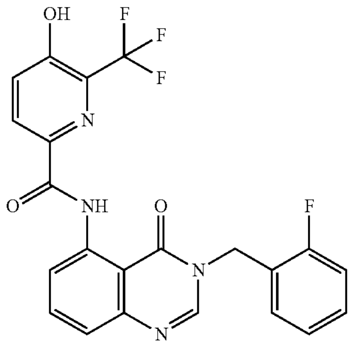 [SMILES: O=C(Nc1cccc2ncn(Cc3ccccc3F)c(=O)c12)c1ccc(O)c(C(F)(F)F)n1] | N-(3-(3,3-dimethylbutyl)-4-oxo-3,4-dihydroquinazolin-5-y1)-6-hydroxy-5-(4-methylpiperazin-1-yl)nicotinamide |
| 5 | 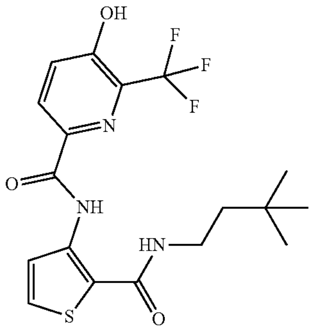 [SMILES: CC(C)(C)CCNC(=O)c1sccc1NC(=O)c1ccc(O)c(C(F)(F)F)n1] | N-(2-((3,3-dimethylbutyl)carbamoyl) thiophen-3-y1)-5-hydroxy-6-(trifluoromethyl) picolinamide |
| 6 | 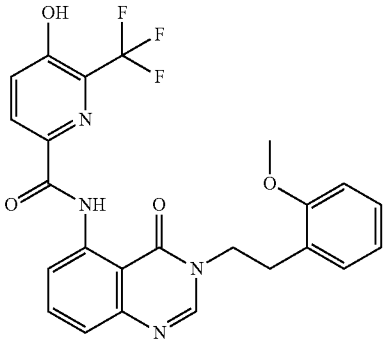 [SMILES: COc1ccccc1CCn1cnc2cccc(NC(=O)c3ccc(O)c(C(F)(F)F)n3)c2c1=O] | 5-hydroxy-N-(3-(2-methoxyphenethyl)-4-oxo-3,4-dihydroquinazolin-5-yl)-6-(trifluoromethyl) picolinamide |

TABLE 1-continued

| Exemplary compounds | | |
|---|---|---|
| Ex. | Structure | Name |
| 7 | 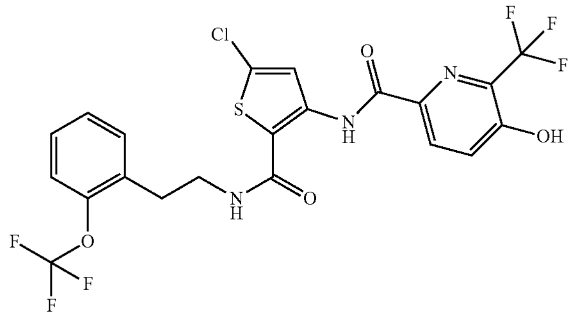 [SMILES: O=C(Nc1cc(Cl)sc1C(=O)NCCc1ccccc1OC(F)(F)F)c1ccc(O)c(C(F)(F)F)n1] | N-(5-chloro-2-((2-(trifluoromethoxy)phenethyl)carbamoyl)thiophen-3-yl)-5-hydroxy-6-(trifluoromethyl)picolinamide |

Further Forms of Compounds Disclosed Herein

Isomers/Stereoisomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred. In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds disclosed herein include isotopes of hydrogen, carbon, nitrogen, oxygen, phosphorous, sulfur, fluorine and chloride, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and the pharmaceutically acceptable salts, solvates, or stereoisomers thereof which contain the aforementioned isotopes and/or other isotopes of other atoms are within the scope of this invention. Certain isotopically-labeled compounds, for example those into which radioactive isotopes such as $^{3}H$ and $^{14}C$ are incorporated, are useful in drug and/or substrate tissue distribution assays. Tritiated, i.e., $^{3}H$ and carbon-14, i.e., $^{14}C$, isotopes are particularly preferred for their case of preparation and detectability. Further, substitution with heavy isotopes such as deuterium, i.e., $^{2}H$, produces certain therapeutic advantages resulting from greater metabolic stability, for example increased in vivo half-life or reduced dosage requirements.

In some embodiments, the compounds described herein are labeled by other means, including, but not limited to, the use of chromophores or fluorescent moieties, bioluminescent labels, or chemiluminescent labels.

In some embodiments, the labeled compounds described herein are used for measuring in vitro and in vivo binding of unlabeled HSD17B13 inhibitors.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds disclosed herein, or a solvate, or stereoisomer thereof, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylateundeconate and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining the compounds disclosed herein, solvate, or stereoisomer thereof and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+(C_{1-4}\ alkyl)_4$, and the like.

Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Tautomers

In some situations, compounds exist as tautomers. The compounds described herein include all possible tautomers within the formulas described herein. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH.

Method of Treatment

Provided herein are methods of inhibiting HSD17B13 expression or activity, which can be useful for treating, preventing, or ameliorating a disease associated with HSD17B13 in a subject in need thereof, such as NAFLD or NASH, by administration of a compound that targets HSD17B13, or a pharmaceutically acceptable salt, solvate, or stereoisomer thereof.

Provided herein are methods of inhibiting expression or activity of HSD17B13 in a cell comprising contacting the cell with a HSD17B13 inhibitor disclosed or a pharmaceutically acceptable salt, solvate, or stereoisomer thereof, thereby inhibiting expression or activity of HSD17B13 in the cell. In some embodiments, the cell is a hepatocyte cell. In some embodiments, the cell is in the liver. In some embodiments, the cell is in the liver of a subject who has, or is at risk of having a disease, disorder, condition, symptom, or physiological marker associated with a liver disease, metabolic disease, or cardiovascular disease or disorder. In some embodiments, the cells are the adipocytes or monocytes from a subject who has or is at risk of having a disease. In some embodiments, the cells are the lymphocytes from a subject who has or is at risk of having a disease. In some embodiments, the liver disease, metabolic disease, or cardiovascular disease or disorder is metabolic syndrome, fatty liver disease, chronic liver disease, liver cirrhosis, hepatic steatosis, steatohepatitis, nonalcoholic fatty liver disease (NAFLD), alcoholic liver disease, nonalcoholic steatohepatitis (NASH), fulminant Wilson's disease, rapidly fibrosing hepatitis C viral injury, and decompensated portal vein hypertension. In some embodiments, the liver disease, metabolic disease, or cardiovascular disease or disorder is NASH.

In some embodiments, the liver disease is primary biliary cirrhosis or primary sclerosing cholangitis.

Provided herein are methods of treating, preventing, delaying the onset, slowing the progression, or ameliorating one or more diseases, disorders, conditions, symptoms, or physiological markers associated with HSD17B13 comprising administering to a subject in need thereof a compound disclosed herein, or a pharmaceutically acceptable salt, solvate, or stereoisomer thereof. In some embodiments, the subject in need thereof is identified as having, or at risk of having, the disease, disorder, condition, symptom or physiological marker. In some embodiments, the liver disease, metabolic disease, or cardiovascular disease or disorder is metabolic syndrome, liver disease, fatty liver disease, chronic liver disease, liver cirrhosis, hepatic steatosis, steatohepatitis, alcoholic liver disease, nonalcoholic fatty liver disease (NAFLD), and nonalcoholic steatohepatitis (NASH). In some embodiments, the liver disease, metabolic disease, or cardiovascular disease or disorder is NASH.

Provided herein are methods of reducing, improving, or regulating hepatic steatosis, liver fibrosis, triglyceride synthesis, lipid levels, hepatic lipids, ALT levels, NAFLD Activity Score (NAS), cholesterol levels, or triglyceride levels, or a combination thereof, in a subject in need thereof comprising administering to the subject a compound disclosed herein, or a pharmaceutically acceptable salt, solvate, or stereoisomer thereof. In some embodiments, the compound disclosed herein, or a pharmaceutically acceptable salt, solvate, or stereoisomer thereof, is provided for use in reducing, improving, or regulating hepatic steatosis in the individual. In some embodiments, the compound disclosed herein, or a pharmaceutically acceptable salt, solvate, or stereoisomer thereof, is provided for use in reducing, improving, or regulating liver fibrosis in the individual. In some embodiments, the compound disclosed herein, or a pharmaceutically acceptable salt, solvate, or stereoisomer thereof, is provided for use in reducing, improving, or regulating triglyceride synthesis in the individual. In some embodiments, the compound disclosed herein, or a pharmaceutically acceptable salt, solvate, or stereoisomer thereof, is provided for use in reducing, improving, or regulating lipid levels in the individual. In some embodiments, the compound disclosed herein, or a pharmaceutically acceptable salt, solvate, or stereoisomer thereof, is provided for use in reducing, improving, or regulating hepatic lipids in the individual. In some embodiments, the compound disclosed herein, or a pharmaceutically acceptable salt, solvate, or stereoisomer thereof, is provided for use in reducing, improving, or regulating ALT levels in the individual. In some embodiments, the compound disclosed herein, or a pharmaceutically acceptable salt, solvate, or stereoisomer thereof, is provided for use in reducing, improving, or regulating NAFLD Activity Score in the individual. In some embodiments, the compound disclosed herein, or a pharmaceutically acceptable salt, solvate, or stereoisomer thereof, is provided for use in reducing, improving, or regulating cholesterol levels in the individual. In some embodiments, the compound disclosed herein, or a pharmaceutically acceptable salt, solvate, or stereoisomer thereof, is provided for use in reducing, improving, or regulating triglyceride levels in the individual. In some embodiments, the subject is identified as having, or at risk of having a disease, disorder, condition, symptom, or physiological marker associated with a liver disease, metabolic disease, or cardiovascular disease or disorder. In some embodiments, the liver disease, metabolic disease, or cardiovascular disease or disorder is metabolic syndrome, liver disease, fatty liver disease, chronic liver disease, liver cirrhosis, hepatic steatosis, steatohepatitis, nonalcoholic fatty liver disease (NAFLD), and nonalcoholic steatohepatitis (NASH). In some embodiments, the liver disease, metabolic disease, or cardiovascular disease or disorder is NASH.

Provided herein are methods for treating, preventing, or delaying onset drug induced liver injury (DILI) in a subject in need thereof. In some embodiments, the liver injury is steatohepatitis. Also provided herein are methods for treating, preventing, or delaying onset drug induced steatohepatitis (DISH) in a subject in need thereof. In some embodiments, the subject in need thereof is receiving chemotherapy for treating cancer. In some embodiments, the subject in need thereof is receiving a treatment for a cardiovascular disease. In some embodiments, the subject in need thereof is receiving treatment for a psychiatric disease/condition. In some embodiments, the subject in need thereof is receiving treatment for pain. In some embodiments, the subject in need thereof is receiving treatment for arthritis. In some embodiments, the chemotherapy is tamoxifen, toremifene, irinotecan, methotrexate, fluorouracil (5-FU), or any combination thereof. In some embodiments, the subject in need thereof is receiving amiodarone, perhexiline, propranolol, or any combination thereof. In some embodiments, the subject in need thereof is receiving amitriptyline, clozapine, or any combination thereof. In some embodiments, the subject in need thereof is receiving methotrexate, pirprofen, or any combinations thereof.

Dosing

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of or risk factor for the disease being treated and is currently in remission, a pharmaceutical composition comprising a compound described herein, or a pharmaceutically acceptable salt thereof, in order to prevent a return of the symptoms of the disease or condition. In one aspect, prophylactic treatments include administering to a mammal having patatin-like phospholipase domain-containing 3 (PNPLA3) polymorphism, a pharmaceutical composition comprising a compound described herein, or a pharmaceutically acceptable salt thereof, in order to prevent liver damages. The 148 Isoleucine to Methionine protein variant (I148M) of patatin-like phospholipase domain-containing 3 (PNPLA3), a protein is expressed in the liver and is involved in lipid metabolism, has recently been identified as a major determinant of liver fat content. Several studies confirmed that the I148M variant predisposes towards the full spectrum of liver damage associated with fatty liver: from simple steatosis to steatohepatitis and progressive fibrosis. Furthermore, the I148M variant represents a major determinant of progression of alcohol related steatohepatitis to cirrhosis, and to influence fibrogenesis and related clinical outcomes in chronic hepatitis C virus hepatitis, and possibly chronic hepatitis B virus hepatitis, hereditary hemochromatosis and primary sclerosing cholangitis. In some embodiments, PNPLA3 polymorphism is used to predict liver disease progression.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered is temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent or daily treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound described herein, or a pharmaceutically acceptable salt thereof, are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{10}$ and the $ED_{90}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (c) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the subject every 12 hours; (v) the compound is administered to the subject every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

Pharmaceutical Compositions/Formulations

The compounds described herein are administered to a subject in need thereof, either alone or in combination with pharmaceutically acceptable carriers, excipients or diluents, in a pharmaceutical composition, according to standard pharmaceutical practice. In one embodiment, the compounds of this invention may be administered to animals. The compounds can be administered orally or parenterally, including the intravenous, intramuscular, intraperitoneal, subcutaneous, rectal and topical routes of administration.

In another aspect, provided herein are pharmaceutical compositions comprising a compound described herein, or a pharmaceutically acceptable salt, solvate, or stereoisomer thereof, and at least one pharmaceutically acceptable excipient. Pharmaceutical compositions are formulated in a conventional manner using one or more pharmaceutically acceptable excipients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton. Pa.: Mack Publishing Company, 1995); Hoover, John E., Remington's Pharmaceutical Sciences, Mack Publishing Co., Easton, Pennsylvania 1975; Liberman, H. A, and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the pharmaceutically acceptable excipient is selected from carriers, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, and any combinations thereof.

The pharmaceutical compositions described herein are administered to a subject by appropriate administration routes, including, but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, liquids, gels, syrups, elixirs, slurries, suspensions, self-emulsifying dispersions, solid solutions, liposomal dispersions, aerosols, solid oral dosage forms, powders, immediate release formulations, controlled release formulations, fast melt formulations, tablets, capsules, pills, powders, dragees, effervescent formulations, lyophilized formulations, delayed release formulations, extended release formulations, pulsatile release formulations, multiparticulate formulations, and mixed immediate and controlled release formulations.

Pharmaceutical compositions including compounds described herein, or a pharmaceutically acceptable salt, solvate, or stereoisomer thereof are manufactured in a conventional manner, such as, by way of example only, by means of conventional mixing, dissolving, granulating, dragee-making, levigating, emulsifying, encapsulating, entrapping, or compression processes.

Pharmaceutical compositions for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as polyvinylpyrrolidone (PVP or povidone) or calcium phosphate. If desired, disintegrating agents are added, such as the cross-linked croscarmellose sodium, polyvinylpyrrolidone, agar, or alginic acid or a salt thereof such as sodium alginate. In some embodiments, dyestuffs or pigments are added to the tablets or dragee coatings for identification or to characterize different combinations of active compound doses.

Pharmaceutical compositions that are administered orally include push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In soft capsules, the active compounds are dissolved or suspended in suitable liquids, such as fatty oils, liquid paraffin, or liquid polyethylene glycols. In some embodiments, stabilizers are added.

Pharmaceutical compositions for parental use are formulated as infusions or injections. In some embodiments, the pharmaceutical composition suitable for injection or infusion includes sterile aqueous solutions, or dispersions, or sterile powders comprising a compound described herein, or a pharmaceutically acceptable salt, solvate, or stereoisomer thereof. In some embodiments, the pharmaceutical composition comprises a liquid carrier. In some embodiments, the liquid carrier is a solvent or liquid dispersion medium comprising, for example, water, saline, ethanol, a polyol (for example, glycerol, propylene glycol, liquid polyethylene glycols, and the like), vegetable oils, nontoxic glyceryl esters, and any combinations thereof. In some embodiments, the pharmaceutical compositions further comprise a preservative to prevent growth of microorganisms.

Combination

Disclosed herein are method of treating a liver disease, metabolic disease, or cardiovascular disease using a compound disclosed herein, or a pharmaceutically acceptable salt, solvate, or stereoisomer thereof, in combination with an additional therapeutic agent.

In some embodiments, the additional therapeutic agent is used for the treatment of diabetes or diabetes related disorder or conditions.

In some instances, the additional therapeutic agent comprises a statin, an insulin sensitizing drug, an insulin secretagogue, an alpha-glucosidase inhibitor, a GLP agonist, a GIP agonist, a THR beta agonist, a PDE inhibitor, a DPP-4 inhibitor (such as sitagliptin, vildagliptin, saxagliptin, linagliptin, anagliptin, teneligliptin, alogliptin, gemigliptin, or dutogliptin), a catecholamine (such as epinephrine, norepinephrine, or dopamine), peroxisome proliferator-activated receptor (PPAR)-gamma agonist (e.g., a thiazolidinedione (TZD) [such as pioglitazone, rosiglitazone, rivoglitazone, or troglitazone], aleglitazar, farglitazar, muraglitazar, or tesaglitazar), peroxisome proliferator-activated receptor (PPAR)-alpha agonist, peroxisome proliferator-activated receptor (PPAR)-delta agonist, a farnesoid X receptor (FXR) agonist (e.g., obeticholic acid), or a combination thereof. In some cases, the statin is a HMG-CoA reductase inhibitor. In other instances, additional therapeutic agents include fish oil, fibrate, vitamins such as niacin, retinoic acid (e.g., 9 cis-retinoic acid), nicotinamide ribonucleoside or its analogs thereof, or combinations thereof. In other instances, additional therapeutic agents include ACC inhibitors, FGF19 and FGF21 mimics, CCR2/CCR5 antagonists, or combinations thereof.

In some embodiments, the additional therapeutic agent is vivitrol.

In some embodiments, the additional therapeutic agent is a statin such as a HMG-CoA reductase inhibitor, fish oil, fibrate, niacin or a combination thereof. In other instances, the additional therapeutic agent is a dyslipidemia drug that prevent lipid absorption such as orlistat.

In some embodiments, the additional therapeutic agent is a vitamin such as retinoic acid or tocopheryl acetate for the treatment of diabetes and diabetes related disorder or condition such as lowering elevated body weight and/or lowering elevated blood glucose from food intake.

In some embodiments, the additional therapeutic agent is a glucose-lowering agent. In some embodiments, the additional therapeutic agent is an anti-obesity agent. In some embodiments, the additional therapeutic agent is selected from among a peroxisome proliferator activated receptor (PPAR) agonist (gamma, dual, or pan), a dipeptidyl peptidase (IV) inhibitor, a glucagon-like peptide-1 (GLP-I) analog, insulin or an insulin analog, an insulin secretagogue, a sodium glucose co-transporter 2 (SGLT2) inhibitor, a glucophage, a human amylin analog, a biguanide, an alpha-glucosidase inhibitor, a meglitinide, a thiazolidinedione, and sulfonylurea. In some embodiments, the additional therapeutic agent is metformin, sitagliptin, saxagliptin, repaglinide, nateglinide, exenatide, liraglutide, insulin lispro, insulin aspart, insulin glargine, insulin detemir, insulin isophane, and glucagon-like peptide 1, or any combination thereof. In some embodiments, the additional therapeutic agent is a lipid-lowering agent.

In some embodiments, the additional therapeutic agent is an antioxidant, corticosteroid such as budesonide, anti-tumor necrosis factor (TNF), or a combination thereof.

In some embodiments, the additional therapeutic agent is administered at the same time as the compound disclosed herein. In some embodiments, the additional therapeutic agent and the compound disclosed herein are administered sequentially. In some embodiments, the additional therapeutic agent is administered less frequently than the compound disclosed herein. In some embodiments, the additional therapeutic agent is administered more frequently than the compound disclosed herein. In some embodiments, the additional therapeutic agent is administered prior than the administration of the compound disclosed herein. In some embodiments, the additional therapeutic agent is administered after the administration of the compound disclosed herein.

EXAMPLES

Example 1: Synthesis of 5-hydroxy-N-(4-oxo-3-{2-[2-(trifluoromethoxy) phenyl]ethyl}-3,4-dihydroquinazolin-5-yl)-6-(trifluoromethyl)pyridine-2-carboxamide

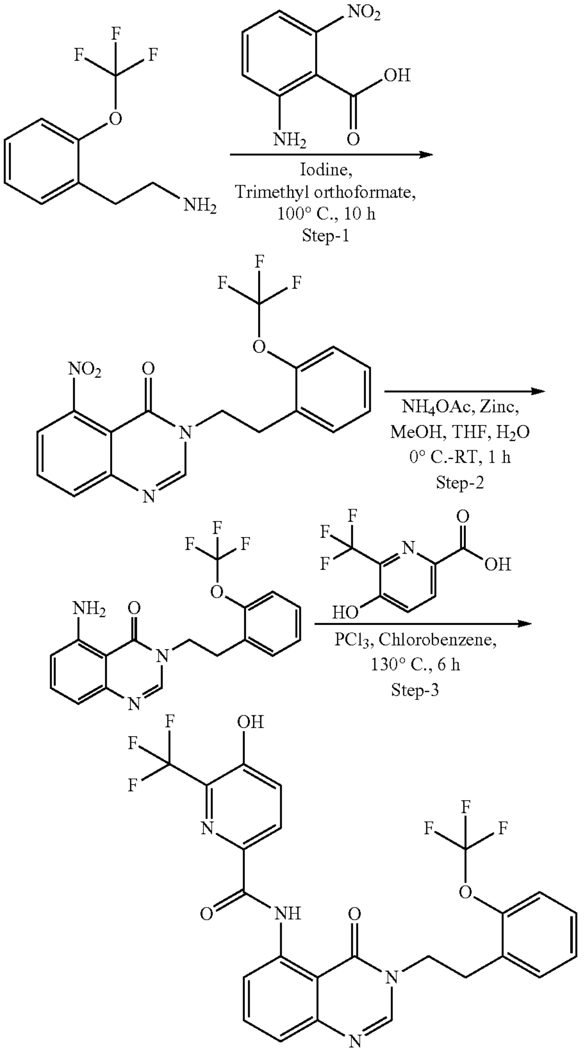

Step 1: Synthesis of 5-nitro-3-{2-[2-(trifluoromethoxy)phenyl]ethyl}-3,4-dihydroquinazolin-4-one To a stirred solution of 1-[2-(trifluoromethoxy)phenyl] methanamine (0.5 g, 2.44 mmol) in trimethyl orthoformate (10 mL) were added 2-amino-6-nitrobenzoic acid (0.66 g, 3.66 mmol) and molecular iodine (0.03 g, 0.244 mmol) at ambient temperature. The resulting reaction mixture was heated to 100° C. for 10 h. After completion of the reaction, the reaction mixture was cooled to ambient temperature and poured into water (25 mL) and extracted with ethyl acetate (2×25 mL). The combined organic layers were washed with brine solution (25 mL) and dried over anhydrous sodium sulfate, filtered and concentrated under vacuo. The crude product was purified by combiflash chromatography using ethyl acetate and n-hexane as a gradient (required product elutes at around 30% ethyl acetate and n-hexane). Purification afforded 5-nitro-3-{2-[2-(trifluoromethoxy)phenyl] ethyl}-3,4-dihydroquinazolin-4-one as a yellow solid (0.92 g, 99% yield). LCMS (ES) m z calcd. C17H12F3N3O4, 379.08: found, 380.1 (M+H).

Step 2: Synthesis of 5-amino-3-{2-[2-(trifluoromethoxy)phenyl]ethyl}-3,4-dihydroquinazolin-4-one To a stirred solution of 5-nitro-3-{2-[2-(trifluoromethoxy) phenyl]ethyl}-3,4-dihydroquinazolin-4-one (1.0 g, 2.64 mmol) in Methanol:Water:Tetrahydrofuran (1:1:4) (25 ml) were added ammonium acetate (2.03 g, 26.4 mmol) and Zinc powder (1.72 g, 26.4 mmol) at ambient temperature. The resulting reaction mixture was stirred at same temperature for 1 h. After completion of the reaction, the reaction mixture was filtered through a pad of celite and the filtrate was diluted with ethyl acetate (30 mL) and washed with water (25 mL), brine solution (25 mL), dried over anhydrous sodium sulfate, filtered and concentrated under vacuo. The crude product was purified by combiflash chromatography using ethyl acetate and n-hexane as a gradient (required product elutes at around 20% ethyl acetate and n-hexane). Purification afforded 5-amino-3-{2-[2-(trifluoromethoxy) phenyl]ethyl}-3,4-dihydroquinazolin-4-one (300 mg, 0.859 mmol) as a yellow solid (0.3 g, 33%). LCMS (ES) m/z calcd. C17H14F3N3O2, 349.1; found, 350.1 (M+H).

Step 3: Synthesis 5-hydroxy-N-(4-oxo-3-{2-[2-(trifluoromethoxy)phenyl] ethyl}-3,4-dihydroquinazolin-5-yl)-6-(trifluoromethyl)pyridine-2-carboxamide To a stirred solution of 5-amino-3-{2-[2-(trifluoromethoxy)phenyl]ethyl}-3,4-dihydroquinazolin-4-one (0.1 g, 0.286 mmol) in chlorobenzene (2.0 mL) was added 5-hydroxy-6-(trifluoromethyl)pyridine-2-carboxylic acid (0.88 g, 0.429 mmol) and Phosphorus trichloride (0.014 mL, 0.14 mmol) at ambient temperature. The resulting reaction mixture was heated to 130° C. for 6 h. After completion of the reaction, the reaction mixture was cooled to ambient temperature and poured into cold water (25 mL). Precipitated solids were filtered and dried under vacuo. The crude was purified by Prep-HPLC (Analytical conditions: Column: X-Bridge C-18 (250 mm×4.6 mm×5 mic); Mobile phase (A): 0.1% TFA in water; Mobile phase (B): Acetonitrile; Flow rate: 1.0 ml/min) to afford 5-hydroxy-N-(4-oxo-3-{2-[2-(trifluoromethoxy)phenyl]ethyl}-3,4-dihydroquinazolin-5-yl)-6-(trifluoromethyl)pyridine-2-carboxamide (0.023 g, 15%) as an off-white solid. LCMS (ES) m/z calcd. C24H16F6N4O4, 538.1; found, 539.1 (M+1). $^1$H NMR (400 MHz, DMSO d6) δ 13.9 (s, 1H), 11.96 (s, 1H), 10.84 (d, J=7.6 Hz, 1H), 8.32 (d, J=8.4 Hz, 1H), 8.20 (s, 1H), 9.82 (t, J=8.4 Hz, 1H), 7.69 (d, J=8.8 Hz, 1H), 7.56-7.53 (m, 1H), 7.38-7.34 (m, 4H), 4.25 (br, 2H), 3.19 (t, J=7.2 Hz, 2H).

Example 2: Synthesis of 5-hydroxy-N-(4-oxo-3-(2-(trifluoromethyl) phenethyl)-3,4-dihydroquinazolin-5-yl)-6-(trifluoromethyl)picolinamide

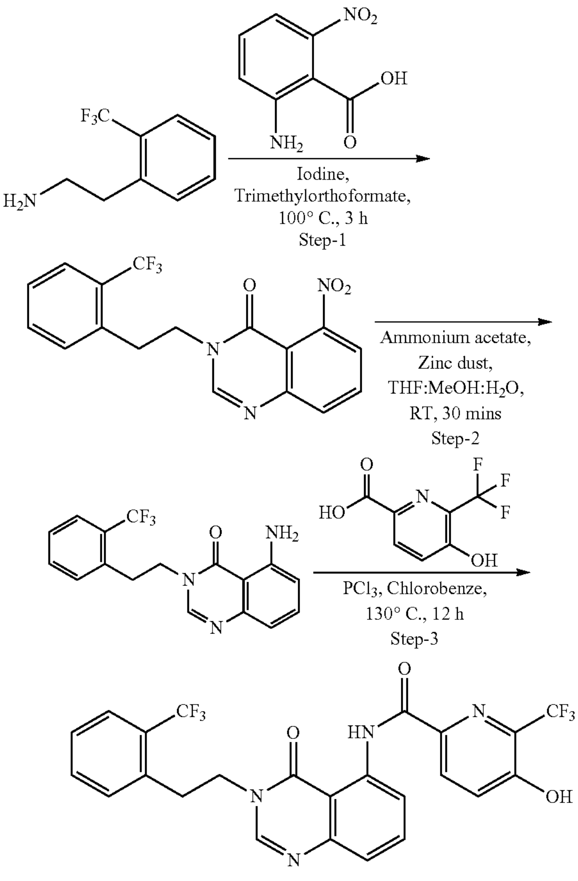

Step 1: 5-nitro-3-(2-(trifluoromethyl)phenethyl)quinazolin-4(3H)-one

To a stirred solution of 1-[2-(trifluoromethyl)phenyl] methanamine (0.4 g, 2.11 mmol) in trimethyl orthoformate (1 mL, 4.23 mmol) were added 2-amino-6-nitrobenzoic acid (0.43 g, 2.33 mmol) and molecular iodine (0.026 g, 0.211 mmol) at ambient temperature. The resulting reaction mixture was heated to 100° C. for 3 h. After completion of the reaction, the reaction mixture was cooled to ambient temperature and poured in to water (25 mL) and extracted with ethyl acetate (2×25 mL). The combined organic layers were washed with brine solution (25 mL) and dried over anhydrous sodium sulfate, filtered and concentrated under vacuo. The crude product was purified by combiflash chromatography using ethyl acetate and n-hexane as a gradient (required product elutes at around 30% ethyl acetate and n-hexane). Purification afforded 5-nitro-3-(2-(trifluoromethyl)phenethyl)quinazolin-4(3H)-one as a yellow solid (0.6 g, 78% yield). LCMS (ES) m/z calcd. C17H12F3N3O3, 363.1; found, 364.1 (M+H).

Step 2: 5-amino-3-(2-(trifluoromethyl)phenethyl) quinazolin-4(3H)-one

To a stirred solution of 5-nitro-3-(2-(trifluoromethyl) phenethyl)quinazolin-4(3H)-one (0.6 g, 1.65 mmol) in Methanol:Water:Tetrahydrofuran (1:1:4) (5 mL) were added ammonium acetate (1.25 g, 16.5 mmol) and Zinc powder (1.0 g, 16.5 mmol) at ambient temperature. The resulting reaction mixture was stirred at same temperature for 30 minutes. After completion of the reaction, the reaction mixture was filtered through a pad of celite and the filtrate was diluted with ethyl acetate (25 mL) and washed with water (20 mL), brine solution (25 mL), dried over anhydrous sodium sulfate, filtered and concentrated under vacuo. The crude product was purified by combiflash chromatography using ethyl acetate and n-hexane as a gradient (required product elutes at around 30% ethyl acetate and n-hexane). Purification afforded 5-amino-3-(2-(trifluoromethyl)phenethyl)quinazolin-4(3H)-one as off-white solid (0.5 g, 90%). LCMS (ES) m/z calcd. C17H14F3N3O, 333.1; found, 334.1 (M+H).

Step 3: 5-hydroxy-N-(4-oxo-3-(2-(trifluoromethyl) phenethyl)-3,4-dihydro quinazolin-5-yl)-6-(trifluoromethyl)picolinamide To a stirred solution of 5-amino-3-(2-(trifluoromethyl) phenethyl)quinazolin-4(3H)-one (0.1 g, 0.33 mmol) in chlorobenzene (3.00 mL) was added 5-hydroxy-6-(trifluoromethyl)pyridine-2-carboxylic acid (0.074 g, 0.360 mmol) and Phosphorus trichloride (0.018 mL, 0.21 mmol) at ambient temperature. The resulting reaction mixture was heated to 130° C. for 12 h. After completion of the reaction, the reaction mixture was cooled to ambient temperature and poured in to water (25 mL) and extracted with ethyl acetate (2×25 mL). The combined organic layers were washed with brine solution (25 mL) and dried over anhydrous sodium sulfate, filtered and concentrated under vacuo. The crude product was purified by combiflash chromatography using 40% ethyl acetate-hexane as a gradient, which was further purified by Prep-HPLC (Analytical conditions: XBridge C18 (150 mm×4.6 mm×5 μm); Mobile phase (A): 0.1% TFA in Water; Mobile phase (B): Acetonitrile; Flow rate: 1.0 ml/min) to afford 5-hydroxy-N-(4-oxo-3-(2-(trifluoromethyl)phenethyl)-3,4-dihydroquinazolin-5-yl)-6-(trifluoromethyl) picolinamide as a white solid (0.021 g, 13%). LCMS (ES) m/z calcd. C24H16F6N4O3, 522.1; found, 523.1 (M+1); $^1$H NMR (400 MHz, DMSO d6) δ 13.78 (s, 1H), 11.98 (s, 1H), 8.85 (d, J=8.0 Hz, 1H), 8.30 (d, J=11.6 Hz, 2H), 7.81 (t, J=8.0 Hz, 1H), 7.70-7.60 (m, 4H), 7.45 (t, J=7.6 Hz, 1H), 7.53 (d, J=8.0 Hz, 1H), 4.22 (t, J=7.2 Hz, 2H), 3.23 (t, J=11.6 Hz, 2H).

Example 3: Synthesis of 5-hydroxy-N-(4-oxo-3-{[2-(trifluoromethoxy) phenyl]methyl}-3,4-dihydroquinazolin-5-yl)-6-(trifluoromethyl)pyridine-2-carboxamide

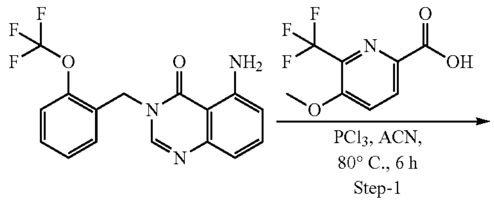

-continued

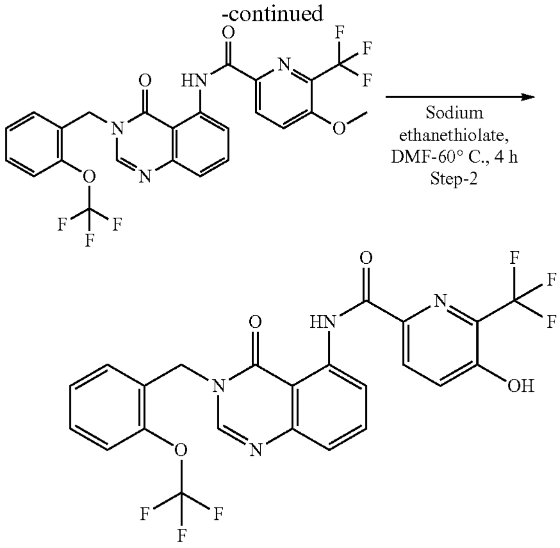

Step 1: Synthesis of 5-methoxy-N-(4-oxo-3-{[2-(trifluoromethoxy)phenyl]methyl}-3,4-dihydroquinazolin-5-yl)-6-(trifluoromethyl)pyridine-2-carboxamide To a stirred solution of 5-amino-3-{[2-(trifluoromethoxy) phenyl]methyl}-3,4-dihydroquinazolin-4-one (0.15 g, 0.447 mmol) in acetonitrile (5.0 mL) was added 5-methoxy-6-(trifluoromethyl)pyridine-2-carboxylic acid (0.15 g, 0.671 mmol) and phosphoryl trichloride (0.022 mL, 0.224 mmol) at ambient temperature and then heated to 80° C. for 6 h. After completion of the reaction, the reaction mixture was poured into cold water (15 mL). Precipitated solid was filtered and dried in vacuo to afford crude 5-methoxy-N-(4-oxo-3-{[2-(trifluoromethoxy)phenyl]methyl}-3,4-dihydroquinazolin-5-yl)-6-(trifluoromethyl) pyridine-2-carboxamide as a brown solid (0.32 g). LCMS (ES) m/z calcd. C24H16F6N4O4, 538.41; found, 539.1 (M+1). The crude compound was taken for next step without any further purification.

Step 2: Synthesis of 5-hydroxy-N-(4-oxo-3-{[2-(trifluoromethoxy) phenyl]methyl}-3,4-dihydroquinazolin-5-yl)-6-(trifluoromethyl)pyridine-2-carboxamide To a stirred solution of 5-methoxy-N-(4-oxo-3-{[2-(trifluoromethoxy)phenyl]methyl}-3,4-dihydroquinazolin-5-yl)-6-(trifluoromethyl)pyridine-2-carboxamide (0.32 g, 0.594 mmol) in N,N-dimethylformamide (5.0 mL) was added sodium ethanethiolate (0.25 g, 2.97 mmol) at ambient temperature and then heated to 60° C. for 4 h. After completion of the reaction, the reaction mixture was poured into ice water (50 ml) and extracted with ethyl acetate (3×20 ml). The combined organic layer was washed with water (10 mL), brine (10 mL), dried over sodium sulfate, filtered and concentrated under vacuo. The crude product was purified by combiflash chromatography using ethyl acetate-hexane as a gradient (required product elutes at around 50% ethyl acetate and n-hexane). Purification afforded 5-hydroxy-N-(4-oxo-3-{[2-(trifluoromethoxy)phenyl]methyl}-3,4-dihydroquinazolin-5-yl)-6-(trifluoromethyl)pyridine-2-carboxamide as a brown solid (17 mg, 6%); LCMS (ES) m/z calcd.: C23H14F6N4O4, 524.09; found, 525.1 (M+1); $^1$H NMR (400 MHz, DMSO d6) δ 13.64 (s, 1H), 12.0 (s, 1H), 8.86 (d, J=7.6 Hz, 1H), 8.54 (s, 1H), 8.26 (d, J=8.4 Hz, 1H), 7.85 (s, 1H), 7.62 (d, J=8.8 Hz, 1H), 7.43 (t, J=5.6 Hz, 5H), 5.30 (s, 2H).

Example 4: Synthesis of N-(3-(2-fluorobenzyl)-4-oxo-3,4-dihydroquinazolin-5-yl)-5-hydroxy-6-(trifluoromethyl)picolinamide

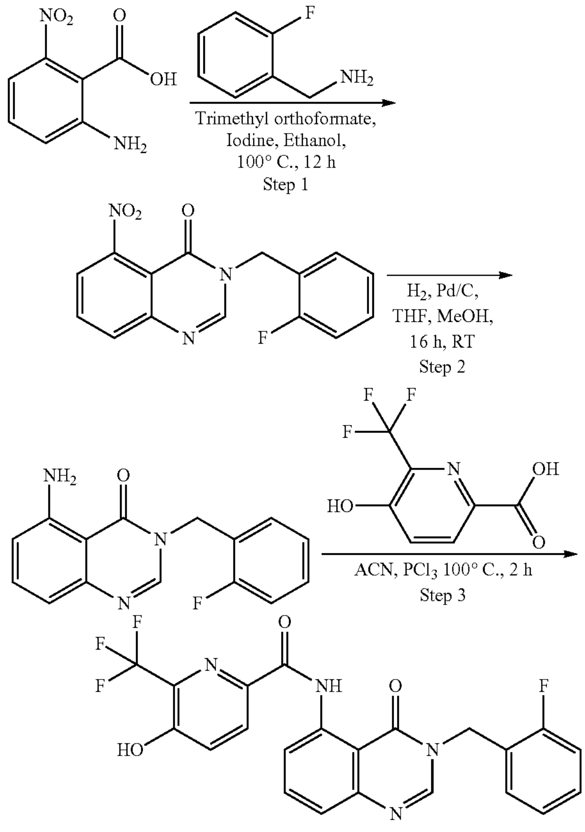

Step 1: Preparation of 3-(2-fluorobenzyl)-5-nitroquinazolin-4(3H)-one

To a stirred solution of 2-amino-6-nitrobenzoic acid (7.00 g, 38.4 mmol) and 1-(2-fluorophenyl) methanamine (5.77 g, 46.1 mmol) in ethanol (50.0 mL) were added trimethoxymethane (9.30 mL, 192 mmol) and iodine (488 mg, 3.84 mmol) at room temperature and the resulting reaction mixture was stirred at 100° C. for 12 hr. The progress of the reaction was monitored by TLC. Upon completion, the reaction mass was poured into sodium thiosulfate and extracted with ethyl acetate (3×50 mL). The combined organic layer was washed with water (2×30 mL) and dried over anhydrous $Na_2SO_4$, filtered and concentrated under reduced pressure to get crude. The crude product was purified through flash column chromatography using Ethyl acetate-hexane gradient (Required product was eluted at 16% ethyl acetate in hexane). The column fractions were combined together and concentrated under reduced pressure to afford desired product (10 g, Yield: 86.95%) as an off brown solid. LCMS (ES) m/z calcd, $C_{15}H_{10}FN_3O_3$, 299, found 300 $(M+H)^+$.

Step 2: Preparation of 5-amino-3-(2-fluorobenzyl) quinazolin-4(3H)-one

To a stirred solution 3-(2-fluorobenzyl)-5-nitroquinazolin-4(3H)-one (5.00 g, 16.7 mmol) in THF (30.0 mL) and methanol (20.0 mL) was added palladium in carbon 10% w/w (1.78 g, 0.1 eq., 1.67 mmol) portion wise. The reaction mixture was stirred under an atmosphere of hydrogen (1 atm) at room temperature for 12 hr. The progress of the reaction was monitored by TLC and LCMS. Upon completion, the reaction mixture was filtered through celite pad, washed with methanol (80 mL) and the filtrate was concentrated under reduced pressure to afford 5-amino-3-(2-fluorobenzyl) quinazolin-4(3H)-one (4 g, 80.61%) as a brown solid. LCMS (ES) m/z calcd, $C_{15}H_{12}FN_3O$, 269, found 270 $[M+H]^+$; $^1H$ NMR (400 MHz, DMSO): δ 8.80 (s, 1H), 7.43 (t, 1H), 7.37-7.29 (m, 3H), 7.23-7.11 (m, 3H) 6.77-6.73 (m, 2H) and 5.16 (s, 2H)

Step-3: N-{3-[(2-fluorophenyl)methyl]-4-oxo-3,4-dihydroquinazolin-5-yl}-5-hydroxy-6-(trifluoromethyl)pyridine-2-carboxamide To a stirred solution of 5-amino-3-(2-fluorobenzyl)quinazolin-4(3H)-one (150 mg, 0.557 mmol) in Acetonitrile (4.00 mL) was added 5-hydroxy-6-(trifluoromethyl)picolinic acid (115 mg, 0.557 mmol) and Phosphorus trichloride (53.5 mg, 0.390 mmol) at ambient temperature and then heated to 130° C. for 2 h. The reaction mixture was cooled to room temperature and diluted with water (20 mL), extracted with 10% MeOH and dichloromethane (2×20 mL). The combined organic layer was washed with water (20 mL), brine (20 mL), dried over sodium sulfate and evaporated under reduced pressure. The crude was purified by flash column chromatography using 10% MeOH and dichloromethane, which was further purified by prep-HPLC (prep conditions: Column: X-Bridge C-18 (19 mm×250 mm×5 μm) Mobile phase (A): 0.1% TFA in Water, Mobile phase (B): Acetonitrile, Flow rate: 19.0 mL/min) to afford N-{3-[(2-fluorophenyl)methyl]-4-oxo-3,4-dihydroquinazolin-5-yl}-5-hydroxy-6-(trifluoromethyl)pyridine-2-carboxamide as off white solid (32.0 mg, 12%). LCMS (ES) m/z calcd. for C22H14F4N4O3, 458.1; found, 459.1 (M+H), $^1H$ NMR (400 MHz, DMSO-$d_6$) δ 13.6 (s, 1H), 11.99 (br, 1H), 8.83 (d, J=8.0 Hz, 1H), 8.56 (s, 1H), 8.26 (d, J=8.8 Hz, 1H), 7.82 (t, J=8.0 Hz, 1H), 7.64 (d, J=8.8 Hz, 1H), 7.45-7.33 (m, 3H), 7.23-7.13 (m, 2H), 5.2 (s, 2H). HPLC purity—99.94% at 260 nm.

Example 5: Synthesis of N-(2-((3,3-dimethylbutyl) carbamoyl)thiophen-3-yl)-5-hydroxy-6-(trifluoromethyl)picolinamide

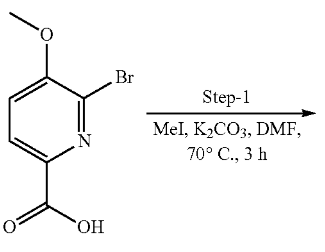

-continued

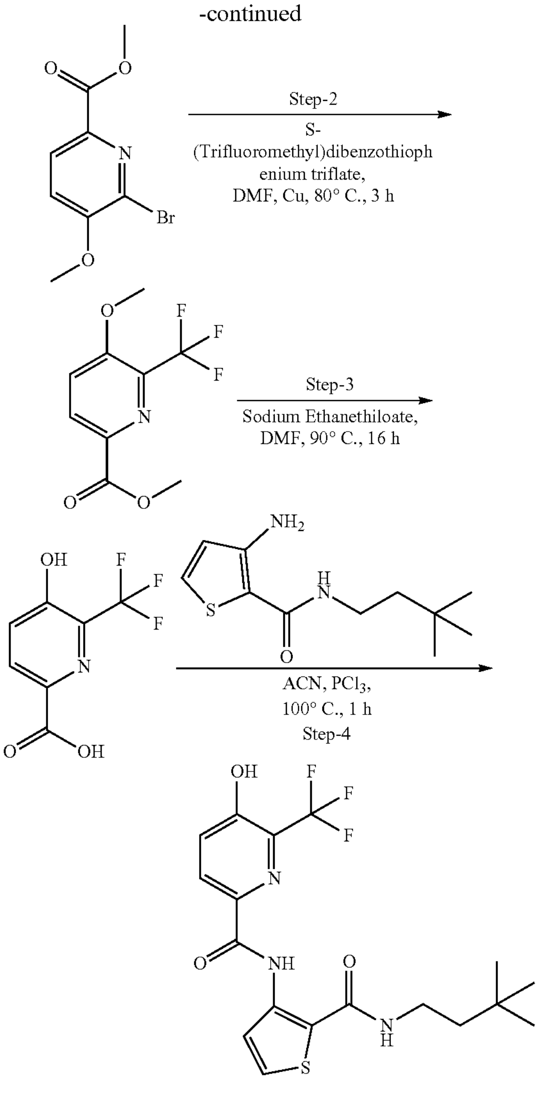

Step-1: Synthesis of methyl 6-bromo-5-methoxypicolinate

To a stirred solution of 6-bromo-3-methoxypyridine-2-carboxylic acid (0.2 g, 0.862 mmol) in N,N-dimethylformamide (3.00 mL) was added potassium carbonate (0.24 g, 1.72 mmol) and iodomethane (0.1 mL, 1.72 mmol) at ambient temperature and then heated to 80° C. for 3 h. After completion of the reaction, the reaction mixture was poured into water (20 mL) and extracted with ethyl acetate (2×20 mL). The organic phase was washed with water, brine solution, dried over anhydrous sodium sulfate, and concentrated under vacuo to afford methyl 6-bromo-5-methoxypicolinate (130 mg, 62%). LCMS (ES) m/z calcd. for $C_8H_8BrNO_3$, 246.0; found, 247 (M+H).

Step-2: Synthesis of methyl 5-methoxy-6-(trifluoromethyl)picolinate

To a stirred solution of methyl 6-bromo-5-methoxypicolinate (0.5 g, 2.03 mmol) in N,N-dimethylformamide (5.0 mL) was added copper powder (387 mg, 3 eq., 6.10 mmol) and Umemoto reagent (1.64 g, 4.06 mmol) at 0-5° C. under nitrogen atmosphere. The resulting reaction mixture was stirred at same temperature for 1 h, and then heated to 80° C. for 3 h. After completion of the reaction, the reaction mixture was poured into water (20 mL) and extracted with ethyl acetate (2×20 mL). The organic phase was washed with water, brine solution, dried over anhydrous sodium sulfate, and concentrated under vacuo, the crude was purified by flash column chromatography using 30% Ethyl acetate and hexane to afford methyl 5-methoxy-6-(trifluoromethyl)picolinate as a white solid (0.4 g, 83%). LCMS (ES) m/z calcd. for $C_9H_8F_3NO_3$, 235.0; found, 236 (M+H).

Step-3: Synthesis of 5-hydroxy-6-(trifluoromethyl)picolinic Acid

To a stirred solution of methyl 5-methoxy-6-(trifluoromethyl)picolinate (0.3 g, 1.28 mmol) in N,N-dimethylformamide (3.0 mL) was added sodium ethane thiolate (0.54 g, 6.38 mmol) and heated to 80° C. for 16 h. After completion of the reaction, the reaction mixture was poured into water (20 mL) and extracted with 10% MeOH and dichloromethane (5×20 mL). The organic phase was washed with water, brine solution, dried over anhydrous sodium sulfate, and concentrated in vacuo to afford 5-hydroxy-6-(trifluoromethyl)picolinic acid (0.25 g, 94%). LCMS (ES) m/z calcd. for $C_7H_4F_3NO_3$, 207.0; found, 208 (M+H).

Step-4: Synthesis of N-(2-((3,3-dimethylbutyl)carbamoyl)thiophen-3-yl)-5-hydroxy-6-(trifluoromethyl)picolinamide To a stirred solution of 3-amino-N-(3,3-dimethylbutyl) thiophene-2-carboxamide (0.1 g, 0.442 mmol) in acetonitrile (2.00 mL) was added 5-hydroxy-6-(trifluoromethyl)picolinic acid (0.095 g, 0.442 mmol) and Phosphorus trichloride (42.5 mg, 0.309 mmol) at ambient temperature and then heated to 130° C. for 2 h. The reaction mixture was cooled to room temperature and diluted with water (20 mL), extracted 10% MeOH and dichloromethane (2×20 mL). The combined organic layer was washed with water (20 mL), brine (20 mL), dried over sodium sulfate and evaporated under reduced pressure. The crude was purified by flash column chromatography using 10% MeOH and dichloromethane, which was further purified by prep-HPLC (prep conditions: Column: X-Bridge C-18 (19 mm×250 mm×5 μm) Mobile phase (A): 0.1% TFA in Water, Mobile phase (B): Acetonitrile, Flow rate: 19.0 mL/min) to afford N-{2-[(3,3-dimethylbutyl)carbamoyl]thiophen-3-yl}-5-hydroxy-6-(trifluoromethyl)pyridine-2-carboxamide (0.038 g, 20%). LCMS (ES) m/z calcd. for $C_{18}H_{20}F_3N_3O_3S$, 415; found, 416 (M+H); $^1$HNMR (400 MHz, DMSO): δ 12.72 (s, 1H), 11.97 (br, 1H), 8.27 (d, J=8.8 Hz, 1H), 8.20-8.15 (m, 2H), 7.74 (d, J=5.2 Hz, 1H), 7.67 (d, J=8.8 Hz, 1H), 3.27-3.24 (m, 2H), 1.49-1.45 (m, 2H), 0.94 (s, 9H). Purity—99.5% at 254 nm Example 6: Synthesis of 5-hydroxy-N-(3-(2-methoxyphenethyl)-4-oxo-3,4-dihydroquinazolin-5-yl)-6-(trifluoromethyl)picolinamide

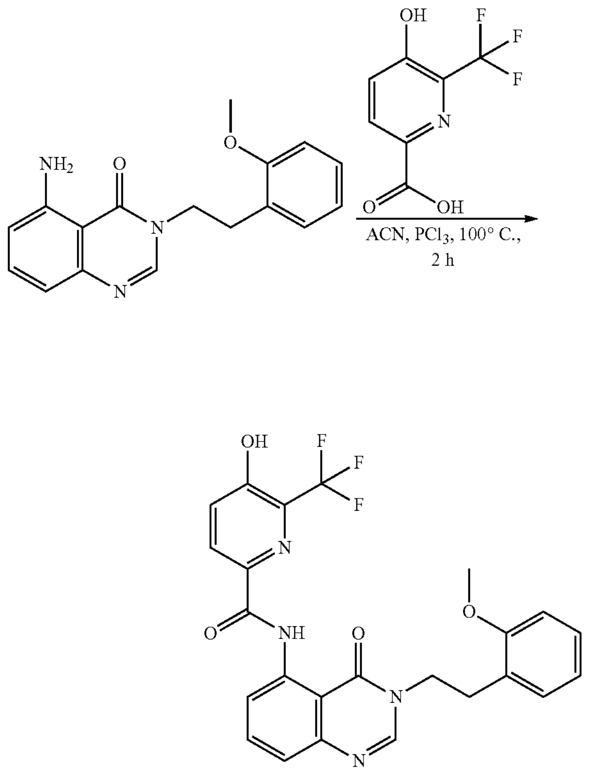

To a stirred solution of 5-amino-3-(2-methoxyphenethyl) quinazolin-4(3H)-one (0.2 g, 0.68 mmol) in Acetonitrile (2.00 mL) was added 5-hydroxy-6-(trifluoromethyl)picolinic acid (141 mg, 0.68 mmol) and Phosphorus trichloride (65.3 mg, 0.47 mmol)) at ambient temperature and then heated to 130° C. for 2 h. The reaction mixture was cooled to room temperature and diluted with water (20 mL), extracted with 10% MeOH and dichloromethane (2×20 mL). The combined organic layer was washed with water (20 mL), brine (20 mL), dried over sodium sulfate and evaporated under reduced pressure. The crude was purified by flash column chromatography using 10% MeOH and dichloromethane, which was further purified by prep-HPLC (Prep conditions: Column: X-Bridge C-18 (19 mm×250 mm×5 μm) Mobile phase (A): 0.1% TFA in Water, Mobile phase (B): Acetonitrile, Flow rate: 19.0 mL/min) to afford 5-hydroxy-N-(3-(2-methoxyphenethyl)-4-oxo-3,4-dihydroquinazolin-5-yl)-6-(trifluoromethyl)picolinamide as a white solid (0.017 g, 5%). LCMS (ES) m/z calcd. for $C_{24}H_{19}F_3N_4O_4$ 484.1; found, 485.2 (M+H). 1HNMR (400 MHz, DMSO): δ 13.8 (s, 1H), 12.02 (s, 1H), 8.84 (d, J=8.4 Hz, 1H), 8.30 (d, J=8.4 Hz, 1H), 7.97 (s, 1H), 7.79 (t, J=7.6 Hz, 1H), 7.68 (d, J=8.8 Hz, 1H), 7.30 (d, J=8.4 Hz, 1H), 7.21-7.12 (m, 2H), 6.90 (d, J=8.4 Hz, 1H), 6.84 (t, J=6.8 Hz, 1H), 4.18 (t, J=6 Hz, 2H), 3.57 (s, 3H), 3.02 (t, J=6.4 Hz, 2H). Purity 99.8% at 254 nm.

Example 7: Synthesis of N-(5-chloro-2-((2-(trifluoromethoxy)phenethyl)carbamoyl) thiophen-3-yl)-5-hydroxy-6-(trifluoromethyl)picolinamide

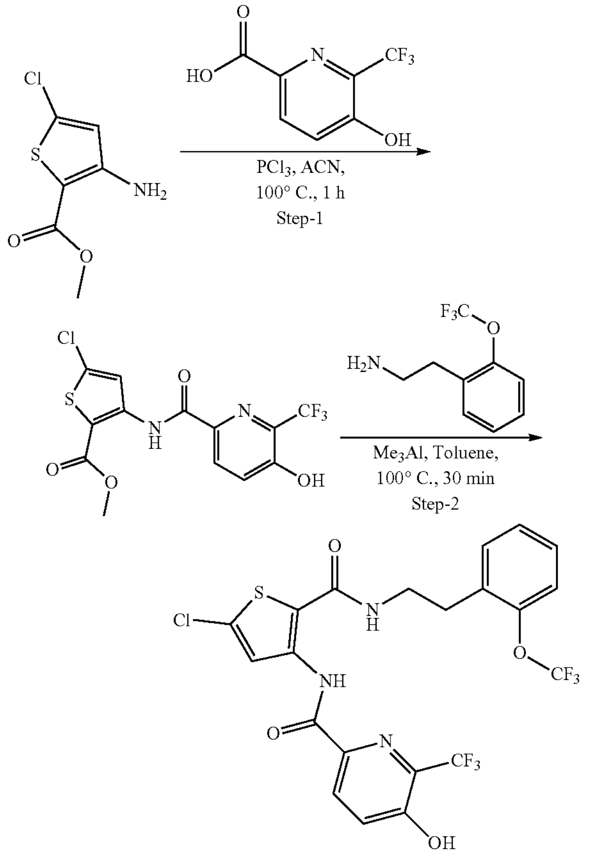

Step 1: Synthesis of methyl 5-chloro-3-(5-hydroxy-6-(trifluoromethyl) picolinamido)thiophene-2-carboxylate To a solution of methyl 3-amino-5-chlorothiophene-2-carboxylate (200 mg, 1.04 mmol) in acetonitrile (5.00 mL) was added 5-hydroxy-6-(trifluoromethyl)picolinic acid (259 mg, 1.25 mmol) and phosphoryl trichloride (0.091 mL, 1.04 mmol) at ambient temperature and then heated to 100° C. for 1 h. The reaction mixture was cooled to room temperature and diluted with water (20 mL), extracted with 5% MeOH and dichloromethane (2×20 mL). The combined organic layer was washed with water (20 mL), brine (20 mL), dried over sodium sulfate and evaporated under reduced pressure. The crude was purified by flash column chromatography using 4% MeOH and dichloromethane gradient to afford methyl 5-chloro-3-(5-hydroxy-6-(trifluoromethyl)picolinamido)thiophene-2-carboxylate (0.13 g, 33%) as off-white solid. MS (ES) m/z: 381.0 (M+H).

Step-2: Synthesis of N-(5-chloro-2-((2-(trifluoromethoxy)phenethyl) carbamoyl)thiophen-3-yl)-5-hydroxy-6-(trifluoromethyl)picolinamide To a suspension of methyl 5-chloro-3-(5-hydroxy-6-(trifluoromethyl)picolinamido)thiophene-2-carboxylate (50.0 mg, 0.137 mmol) in toluene was added 2-[2-(trifluoromethoxy)phenyl]ethan-1-amine (30 mg, 0.144 mmol) and 2M solution of trimethylaluminum in toluene (0.19 mL, 0.39 mmol). The resulting reaction mixture was heated to 100° C. for 30 minutes. The reaction mixture was cooled to room temperature and diluted with water (20 mL), extracted with ethyl acetate (2×20 mL). The combined organic layer was washed with water (20 mL), brine (20 mL), dried over sodium sulfate and evaporated under vacuo. The crude was purified by prep-HPLC (prep condition: Column: Inertsil C18 (19 mm×250 mm×5 mic), Mobile phase (A): 0.1% TFA in water, Mobile phase (B): ACN, Flow rate: 19 mL/min) to afford N-(5-chloro-2-((2-(trifluoromethoxy)phenethyl)carbamoyl)thiophen-3-yl)-5-hydroxy-6-trifluoromethyl) picolinamide (5.0 mg, 6%) as a white solid. LCMS (ES) m/z calcd. for $C_{21}H_{14}ClF_6N_3O_4S$, 553.03; found, 554 (M+H). 1HNMR (400 MHz, DMSO-$d_6$): δ 12.67 (s, 2H), 8.43 (t, J=5.6 Hz, 1H), 8.20 (d, J=8.8 Hz, 1H), 8.15 (s, 1H), 7.61 (d, J=8.0 Hz, 2H), 7.48-7.27 (m, 3H), 3.46 (t, J=16.4 Hz, 2H), 2.90 (t, J=7.6 Hz, 2H). HPLC purity—99.9% at 254 nm.

Example A: Estrone Detection Assay for Evaluation of HSD17ß13 Activity and Identification of Inhibitors The liquid chromatography/mass spectrometry (LC/MS) estrone detection assay monitors the conversion of estradiol to estrone by HSD17B13. This assay was undertaken in a 96 wp format (Eppendorf deep well Plate 96/500) in an 80 μl reaction volume containing: 4 μM of Estradiol (E2; Cayman; #10006315), 6 mM NAD (Sigma; #N0623) and 30 nM HSD17B13 enzyme (in-house; *E. coli* expressed His-tagged, purified, soluble protein) in a reaction containing 1M potassium phosphate buffer pH 7.4, with 0.5% vehicle (DMSO). Reactions were incubated for 2 hours at 26.5° C., and estradiol (E2) conversion to estrone (E1) was quantitated by LC-MS/MS based analyte detection for both E2 and E1 using LCMS grade reagents.

Reactions were terminated by the addition of two volumes of acetonitrile (MeCN: LCMS grade; CAS #75/05/8) containing deuterated (D4)-E1 used as internal standard (Clear Synth: #CS-T-54273; 500 ng/ml final concentration). Samples were applied to pre-prepared Bond Elut-C18 extraction cartridges (3 mL; Agilent; #12102028), washed and eluted in MeCN. Eluates were dried under nitrogen and re-suspended in 60% methanol (LCMS grade methanol; CAS #67/56/1) before submission for analysis. Aqueous linearity for E2 and E1 were included for quantification.

Analysis of samples was undertaken on a XBridge BEH C18 column (Waters; #186003033) using 0.1% Diethyl Amine in MeCN (mobile phase A; DEA CAS #109-89-7) and 0.1% Diethyl Amine in milli-Q water (mobile phase B) in a 3 min gradient allowing 25% B. Analytes were detected in negative mode using MRM analysis, with E2 having a RT of 1.85 min and E1 having a RT of 2 min. Activity of the enzyme, in the absence of $NAD^+$, was used to evaluate specificity of conversion. Enzyme activity in the presence of test samples was expressed as a percentage of the uninhibited enzyme activity, and plotted versus inhibitor concentration. Non-linear regression was performed using a four-parameter logistic model and GraphPad Prism software (GraphPad Software, La Jolla, CA). All assessments were undertaken in duplicate evaluations and pooled during extraction process and subsequently injected as duplicates for LC-MS/MS analysis.

The data is shown in table 2 below:

TABLE 2

| Ex. | $IC_{50}$ with Estradiol (μM) |
|---|---|
| 1 | A |
| 2 | B |
| 3 | A |
| 4 | A |
| 5 | A |
| 6 | A |
| 7 | B |

$IC_{50}$ with Estradiol
A is less than or equal to 0.1 μM;
B is more than 0.1 μM and less than or equal to 0.5 μM;
C is more than 0.5 μM and less than or equal to 1.0 μM;
D is more than 1.0 μM and less than or equal to 10 μM;
E is more than 10 μM;
NT: not tested

What is claimed is:

1. A compound of Formula (I), or a pharmaceutically acceptable salt, solvate, or stereoisomer thereof:

Formula (II)

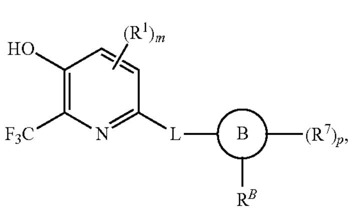

wherein:

each $R^1$ is hydrogen;

m is 1 or 2;

L is —C(═O)$NR^2$— or —$NR^2$C(═O)—;

$R^2$ is hydrogen, —C(═O)$R^a$, $C_1$-$C_6$alkyl, $C_1$-$C_6$ haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

Ring B is cycloalkyl, heterocycloalkyl, aryl, or heteroaryl;

$R^B$ is hydrogen, deuterium, halogen, —CN, —OH, —$OR^{10}$, —OC(═O)$R^{10}$, —OC(═O)$OR^{11}$, —OC(═O)$NR^{12}R^{13}$, —S(═O)$R^{10}$, —S(═O)$_2R^{10}$, —S(═O)$_2NR^{12}R^{13}$, —$NR^{12}R^{13}$, —$NR^{11}$C(═O)$NR^{12}R^{13}$, —$NR^{11}$C(═O)$R^{10}$, —$NR^{11}$C(═O)$OR^{11}$, —$NR^{11}$S(═O)$_2R^{10}$, —C(═O)$R^{10}$, —C(═O)$OR^{11}$, —C(═O)$NR^{12}R^{13}$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl)aryl, or ($C_1$-$C_6$alkyl)heteroaryl; wherein the alkyl, alkenyl, alkynyl, cycloalkyl, heterocycloalkyl, aryl, and heteroaryl is optionally and independently substituted with one or more $R^{Ba}$;

each $R^{Ba}$ is independently deuterium, halogen, —CN, —OH, —$OR^{10}$, —OC(═O)$R^{10}$, —OC(═O)$OR^{11}$, —OC(═O)$NR^{12}R^{13}$, —S(═O)$R^{10}$, —S(═O)$_2R^{10}$, —S(═O)$_2NR^{12}R^{13}$, —$NR^{12}R^{13}$, —$NR^{11}$C(═O)$NR^{12}R^{13}$, —$NR^{11}$C(═O)$R^{10}$, —$NR^{11}$C(═O)$OR^{11}$, —$NR^{11}$S(═O)$_2R^{10}$, —C(═O)$R^{10}$, —C(═O)$OR^{11}$, —C(═O)$NR^{12}R^{13}$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl)aryl, or ($C_1$-$C_6$alkyl)heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(═O)$CH_3$, —S(═O)$_2CH_3$, —S(═O)$_2NH_2$, —S(═O)$_2NHCH_3$, —S(═O)$_2N(CH_3)_2$, —$NH_2$, —$NHCH_3$, —$N(CH_3)_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or two $R^{Ba}$ on the same atom form an oxo;

each $R^7$ is independently hydrogen, deuterium, halogen, —CN, —$NO_2$, —OH, —$OR^a$, —OC(═O)$R^a$, —OC(═O)$OR^b$, —OC(═O)$NR^cR^d$, —SH, —$SR^a$, —S(═O)$R^a$, —S(═O)$_2R^a$, —S(═O)$_2NR^cR^d$, —$NR^cR^d$, —$NR^b$C(═O)$NR^cR^d$, —$NR^b$C(═O)$R^a$, —$NR^b$C(═O)$OR^b$, —NHS(═O)$_2R^a$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^7$ are taken together to form a cycloalkyl, heterocycloalkyl, aryl, or heteroaryl; wherein the cycloalkyl, heterocycloalkyl, aryl, and heteroaryl is optionally substituted with one or more oxo, deuterium, halogen, —CN, —OH, —$OCH_3$, —S(═O)$CH_3$, —S(═O)$_2CH_3$, —S(═O)$_2NH_2$, —S(═O)$_2NHCH_3$, —S(═O)$_2N(CH_3)_2$, —$NH_2$, —$NHCH_3$, —$N(CH_3)_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$ hydroxyalkyl, $C_1$-$C_6$aminoalkyl, or $C_1$-$C_6$heteroalkyl;

or two $R^7$ are taken together to form an oxo;

p is 1-4;

each $R^{10}$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl)aryl, or ($C_1$-$C_6$alkyl)heteroaryl; wherein the alkyl, alkenyl, alkynyl, cycloalkyl, heterocycloalkyl, aryl, and heteroaryl is optionally and independently substituted with one or more $R^{10a}$;

each $R^{11}$ is independently hydrogen, $C_1$-$C_6$alkyl, $C_1$-$C_6$haloalkyl, $C_1$-$C_6$deuteroalkyl, $C_1$-$C_6$ hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl)aryl, or ($C_1$-$C_6$alkyl)heteroaryl; wherein the alkyl, alkenyl, alkynyl, cycloalkyl, heterocycloalkyl, aryl, and heteroaryl is optionally and independently substituted with one or more $R^{11a}$;

each $R^{12}$ and $R^{13}$ are independently hydrogen, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_1$-$C_6$ heteroalkyl, $C_2$-$C_6$alkenyl, $C_2$-$C_6$alkynyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl)aryl, or ($C_1$-$C_6$alkyl)heteroaryl; wherein the alkyl, alkenyl, alkynyl, cycloalkyl, heterocycloalkyl, aryl, and heteroaryl is optionally and independently substituted with one or more $R^{12a}$;

or $R^{12}$ and $R^{13}$ are taken together with the atom to which they are attached to form a heterocycloalkyl optionally substituted with one or more $R^{12b}$;

each $R^{10a}$, $R^{11a}$, $R^{12a}$, or $R^{12b}$ are independently deuterium, halogen, —CN, —$NO_2$, —OH, —$OR^a$, —OC(═O)$R^a$, —OC(═O)$OR^b$, —OC(═O)$NR^cR^d$, —SH, —$SR^a$, —S(═O)$R^a$, —S(═O)$_2R^a$, —S(═O)$_2NR^cR^d$, —$NR^cR^d$, —$NR^b$C(═O)$NR^cR^d$, —$NR^b$C(═O)$R^a$, —$NR^b$C(═O)$OR^b$, —NHS(═O)$_2R^a$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$ hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(═O)$CH_3$, —S(═O)$_2CH_3$, —S(═O)$_2NH_2$, —S(═O)$_2NHCH_3$, —S(═O)$_2N(CH_3)_2$, —$NH_2$, —$NHCH_3$, —$N(CH_3)_2$, —C(═O)$CH_3$, —C(═O)OH, —C(═O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$ aminoalkyl, or $C_1$-$C_6$heteroalkyl;

or two $R^{10a}$, or two $R^{11a}$, or two $R^{12a}$, or two $R^{12b}$ on the same atom are taken together to form an oxo;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$ aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one, two, or three deuterium, oxo, halogen, —CN, —OH, —OMe, —S(═O)Me, —S(═O)$_2$Me, —$NH_2$, —S(═O)$_2NH_2$, —C(═O)Me, —C(═O)OH, —C(═O)OMe, $C_1$-$C_6$alkyl, $C_1$-$C_6$deuteroalkyl, $C_1$-$C_6$haloalkyl, $C_1$-$C_6$ hydroxyalkyl, $C_1$-$C_6$aminoalkyl, or $C_1$-$C_6$heteroalkyl;

each $R^b$ is independently hydrogen, $C_1$-$C_6$alkyl, $C_1$-$C_6$haloalkyl, $C_1$-$C_6$deuteroalkyl, $C_1$-$C_6$ hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one, two, or three deuterium, oxo, halogen, —CN, —OH, —OMe, —S(═O)Me, —S(═O)$_2$Me, —$NH_2$, —S(═O)$_2NH_2$, —C(═O)Me, —C(═O)OH, —C(═O)OMe, $C_1$-$C_6$alkyl, $C_1$-$C_6$haloalkyl, $C_1$-$C_6$deuteroalkyl, $C_1$-$C_6$hydroxyalkyl, $C_1$-$C_6$ aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one, two, or three oxo, deuterium, halogen, —CN, —OH, —OMe, —S(═O)Me, —S(═O)$_2$Me, —$NH_2$, —S(═O)$_2NH_2$, —C(═O)Me, —C(═O)OH, —C(═O)OMe, $C_1$-$C_6$alkyl, $C_1$-$C_6$haloalkyl, $C_1$-$C_6$deuteroalkyl, $C_1$-$C_6$hydroxyalkyl, $C_1$-$C_6$ aminoalkyl, or $C_1$-$C_6$heteroalkyl;

or $R^c$ and $R^d$ are taken together with the atom to which they are attached to form a heterocycloalkyl optionally substituted with one, two, or three oxo, deuterium, halogen, —CN, —OH, —OMe, —S(═O)Me, —$S(=O)_2Me$, —$NH_2$, —$S(=O)_2NH_2$, —C(═O)Me, —C(═O)OH, —C(═O)OMe, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl.

2. The compound of claim 1, or a pharmaceutically acceptable salt, solvate, or stereoisomer thereof, wherein:

$R^2$ is hydrogen.

3. The compound of claim 1, or a pharmaceutically acceptable salt, solvate, or stereoisomer thereof, wherein:

Ring B is aryl or heteroaryl.

4. The compound of claim 1, or a pharmaceutically acceptable salt, solvate, or stereoisomer thereof, wherein:

Ring B is 5-membered heteroaryl.

5. The compound of claim 1, or a pharmaceutically acceptable salt, solvate, or stereoisomer thereof, wherein:

Ring B is 6-membered heteroaryl.

6. The compound of claim 1, or a pharmaceutically acceptable salt, solvate, or stereoisomer thereof, wherein:

Ring B is a bicyclic heteroaryl.

7. The compound of claim 1, or a pharmaceutically acceptable salt, solvate, or stereoisomer thereof, wherein:

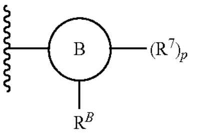

is

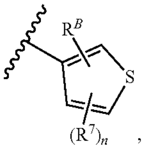

,

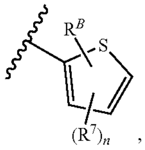

,

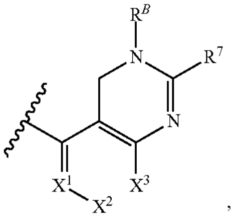

,

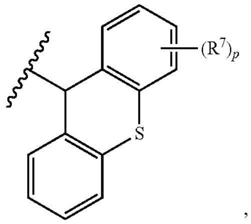

,

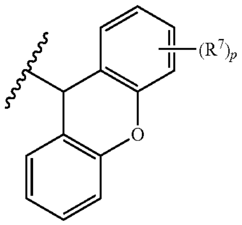

,

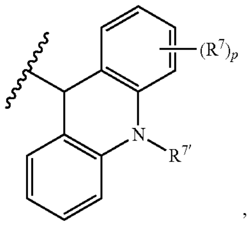

, or

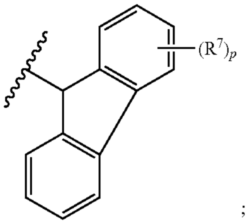

;

wherein $X^1$ is N or $CR^{X1}$;

$R^{X1}$ is hydrogen, deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$ aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

$X^2$ is N or $CR^{X2}$;

$R^{X2}$ is hydrogen, deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$ aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

$X^3$ is N or $CR^{X3}$;

$R^{X3}$ is hydrogen, deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$ aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; and $R^{7'}$ is hydrogen or $C_1$-$C_6$alkyl.

8. The compound of claim 1, or a pharmaceutically acceptable salt, solvate, or stereoisomer thereof, wherein:

$R^B$ is —C(═O)$R^{10}$, —C(═O)$OR^{11}$, —C(═O)$NR^{12}R^{13}$, $C_1$-$C_6$alkyl, $C_1$-$C_6$haloalkyl, $C_1$-$C_6$deuteroalkyl, cycloalkyl, heterocycloalkyl, aryl, heteroaryl, ($C_1$-$C_6$alkyl)cycloalkyl, ($C_1$-$C_6$alkyl)heterocycloalkyl, ($C_1$-$C_6$alkyl)aryl, or ($C_1$-$C_6$alkyl)heteroaryl; wherein the alkyl, cycloalkyl, heterocycloalkyl, aryl, and heteroaryl is optionally and independently substituted with one or more $R^{Ba}$.

9. The compound of claim 1, or a pharmaceutically acceptable salt, solvate, or stereoisomer thereof, wherein:

$R^B$ is —C(═O)$NR^{12}R^{13}$, $C_1$-$C_6$alkyl, cycloalkyl, or ($C_1$-$C_6$alkyl)aryl; wherein the alkyl, cycloalkyl, and aryl is optionally and independently substituted with one or more $R^{Ba}$.

10. The compound of claim 1, or a pharmaceutically acceptable salt, solvate, or stereoisomer thereof, wherein:

each $R^{Ba}$ is independently deuterium, halogen, —CN, —OH, —$OR^{10}$, —$NR^{12}R^{13}$, $C_1$-$C_6$alkyl, $C_1$-$C_6$ haloalkyl, $C_1$-$C_6$deuteroalkyl, $C_1$-$C_6$hydroxyalkyl, or $C_1$-$C_6$aminoalkyl.

11. The compound of claim 1, or a pharmaceutically acceptable salt, solvate, or stereoisomer thereof, wherein:

each $R^{12}$ and $R^{13}$ are independently hydrogen, $C_1$-$C_6$alkyl, $C_1$-$C_6$haloalkyl, cycloalkyl, ($C_1$-$C_6$alkyl) cycloalkyl, or ($C_1$-$C_6$alkyl)aryl; wherein the alkyl, cycloalkyl, and aryl is optionally and independently substituted with one or more $R^{12a}$.

12. The compound of claim 1, or a pharmaceutically acceptable salt, solvate, or stereoisomer thereof, wherein:

each $R^{12a}$ is independently deuterium, halogen, —OH, —$OR^a$, $C_1$-$C_6$alkyl, or $C_1$-$C_6$haloalkyl.

13. The compound of claim 1, or a pharmaceutically acceptable salt, solvate, or stereoisomer thereof, wherein:

each $R^7$ is independently hydrogen, deuterium, halogen, —OH, or $C_1$-$C_6$alkyl; or two $R^7$ are taken together to form an oxo.

14. The compound of claim 1, or a pharmaceutically acceptable salt, solvate, or stereoisomer thereof, wherein:

p is 1.

15. The compound of claim 1 selected from the group consisting of:

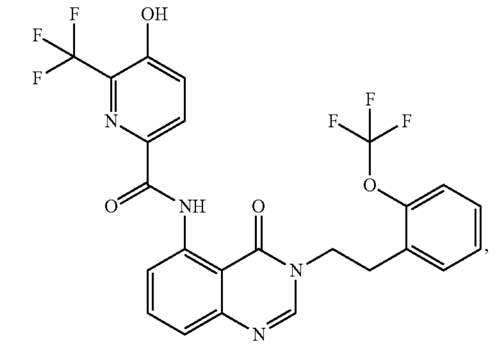

,

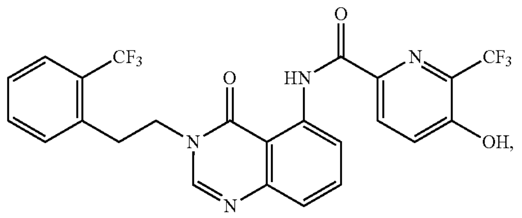

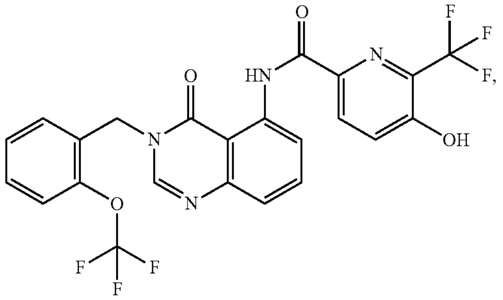

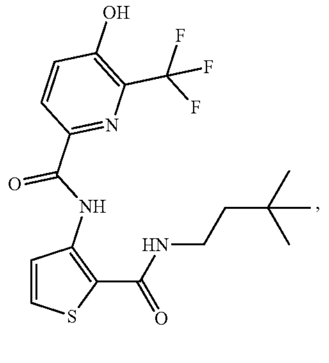

,

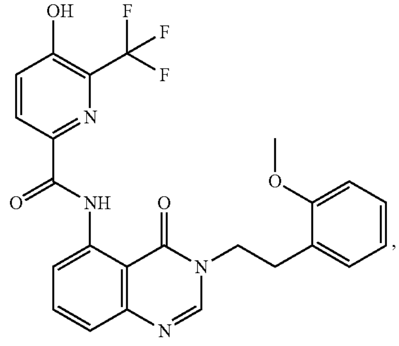

,

-continued

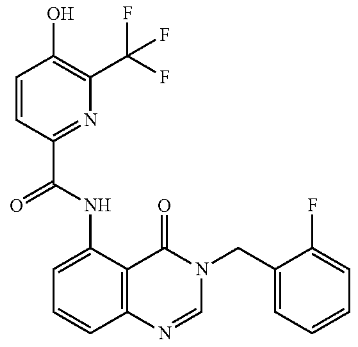

, and

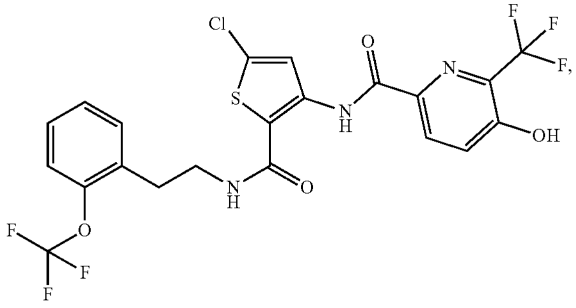

or a pharmaceutically acceptable salt, solvate, or stereoisomer thereof.

16. A pharmaceutical composition comprising a compound of claim 1, or a pharmaceutically acceptable salt, solvate, or stereoisomer thereof, and a pharmaceutically acceptable carrier.

17. A method of treating a liver disease, a metabolic disease, or a cardiovascular disease in a subject in need thereof, the method comprising administering a pharmaceutically effective amount of a compound of claim 1, or a pharmaceutically acceptable salt, solvate, or stereoisomer thereof.

18. The compound of claim 7, or a pharmaceutically acceptable salt, solvate, or stereoisomer thereof, wherein:

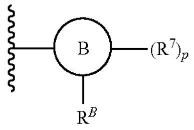

is

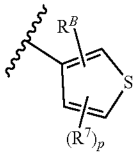

or

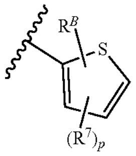

.

19. The compound of claim 7, or a pharmaceutically acceptable salt, solvate, or stereoisomer thereof, wherein:
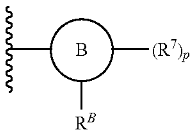
is
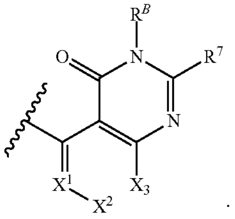
.
20. The compound of claim 19, or a pharmaceutically acceptable salt, solvate, or stereoisomer thereof, wherein:
$X^1$ is $CR^{X1}$ and $R^{X1}$ is hydrogen;
$X^2$ is $CR^{X2}$ and $R^{X2}$ is hydrogen; and
$X^3$ is $CR^{X3}$ and $R^{X3}$ is hydrogen.
* * * * *